US006486122B1

(12) United States Patent
Twardzik et al.

(10) Patent No.: US 6,486,122 B1
(45) Date of Patent: Nov. 26, 2002

(54) METHODS OF INCREASING BODY WEIGHT IN A SUBJECT BY ADMINISTERING TGF-α

(75) Inventors: Daniel R. Twardzik, Bainbridge Island, WA (US); Stefan Paskell, Bainbridge Island, WA (US); Thomas S. Felker, Vashon, WA (US)

(73) Assignee: Stem Cell Pharmaceuticals, Inc., Seattle, WA (US)

( * ) Notice: Subject to any disclaimer, the term of this patent is extended or adjusted under 35 U.S.C. 154(b) by 0 days.

(21) Appl. No.: 09/559,248

(22) Filed: Apr. 26, 2000

Related U.S. Application Data

(63) Continuation-in-part of application No. 09/459,813, filed on Dec. 13, 1999, which is a continuation-in-part of application No. 09/299,473, filed on Apr. 26, 1999.

(51) Int. Cl.$^7$ ........................ A01N 37/18; A61K 38/00; C07K 14/00; C07K 16/00; C07K 17/00
(52) U.S. Cl. ........................ 514/2; 530/300; 530/324
(58) Field of Search ............................. 514/2; 530/300, 530/324

(56) References Cited

U.S. PATENT DOCUMENTS

| | | |
|---|---|---|
| 4,749,683 A | 6/1988 | Murphy et al. |
| 4,816,561 A | 3/1989 | Todaro |
| 4,863,899 A | 9/1989 | Todaro |
| 5,240,912 A | 8/1993 | Todaro |
| 5,633,147 A | 5/1997 | Meissner et al. .......... 435/69.1 |
| 5,814,308 A | 9/1998 | Zhang |
| 5,851,832 A | 12/1998 | Weiss et al. |
| 5,980,885 A | 11/1999 | Weiss et al. |

FOREIGN PATENT DOCUMENTS

| | | | |
|---|---|---|---|
| EP | 0 190 018 A2 * | 1/1986 | |
| WO | WO 91/01141 | 2/1991 | .......... A61K/37/02 |
| WO | WO 97/25349 | 7/1997 | |
| WO | WO 98/24468 | 6/1998 | |

OTHER PUBLICATIONS

Nestor et al., "A Synthetic Fragment of Rat Transforming Growth Factor α With Receptor Binding and Antigenic Properties," *Biochemical and Biophysical Research Communications* 129(1):226–232 (1985).

Chalazonitis et al., "Transforming Growth Factor α, but Not Epidermal Growth Factor, Promotes the Survival of Sensory Neurons in vitro," *The Journal of Neuroscience* 12(2):583–594 (1992).

Coffey et al., "Transforming Growth Factors and Related Peptides in Gastrointestinal Neoplasia," *Journal of Cellular Biochemistry*, Supp.16G:111–118 (1992).

Connor and Dragunow, "The role of neuronal growth factors in neurodegenerative disorders of the human brain," *Brain Research Reviews* 27:1–39 (1998).

Draoui et al., "TGFα–PE40 Inhibits Non–Small Cell Lung Cancer Growth," *Life Sciences* 54(7):445–453 (1994).

Ferrer et al., "Transforming Growth Factor–α (TGF–α) and Epidermal Growth Factor–Receptor (EGF–R) Immunoreactivity in Normal and Pathologic Brain," *Progress in Neurobiology* 49:99–123 (1996).

Jackson et al., "Effects of Transforming Growth Factor β and Interleukin–1β on Expression of Cyclooxygenase 1 and 2 and Phospholipase A$_2$ mRNA in Lung Fibroblasts and Endothelial Cells in Culture," *Biochemical and Biophysical Rsearch Communications* 97(3): 1465–1474 (1993).

Jones et al., "Gastrointestinal Mucosal Regeneration: Role of Growth Factors," *Frontiers in Bioscience* 4:d303–309 (1999).

Liu et al., "TGF–α Can Act as Morphogen and/or Mitogen In a Colon–Cancer Cell Line," *Int. J. Cancer* 56:603–608 (1994).

Liu et al., "Immunohistochemical Study of Transforming Growth Factor–Alpha in Human Lung Cancers," *Tumor Biol.* 13:294–298 (1992).

P. Miettinen, "Transforming Growth Factor–α and Epidermal Growth Factor Expression in Human Fetal Gastrointestinal Tract," *Pediatric Research* 33(5):481–486 (1993).

Mogi et al., "Interleukin–1β, interleukin–6, epidermal growth factor and transforming growth factor–α are elevated in the brain from parkinsonian patients," *Neuroscience Letters* 180:147–150 (1994).

Scheiman et al., "Transforming Growth Factor–Alpha (TGF–α) Levels in Human Proximal Gastrointestinal Epithelium," *Digestive Diseases and Sciences* 42(2):333–341 (1997).

Sottili et al., "Up–regulation of Transforming Growth Factor α Binding Sites in Experimental Rabbit Colitis," *Gastroenterology* 109:24–33 (1995).

Zhang et al., "Transforming growth factor α and a PC–12–derived growth factor induce neurites in PC12 cells and enhance the survival of embryonic brain neurons," *Cell Regulation* 1:511–521 (1990).

* cited by examiner

Primary Examiner—Gary L. Kunz
Assistant Examiner—Robert S. Landsman
(74) Attorney, Agent, or Firm—Gray Cary Ware & Friedenrich LLP; Lisa A. Haile; Kelly K. Reynolds

(57) ABSTRACT

Disclosed are peptides related to human TGF-α, having TGF-α biological activity, which are useful for many of the indications that full-length TGF-α polypeptide is useful. Also provided are methods of use of such peptides, as well as human TGF-α and biologically related polypeptides. For example, methods for treating or preventing cachexia in subjects are provided as well as methods for stimulating hematopoiesis in patients undergoing cytotoxic chemotherapy. In addition, the use of TGF-α related peptides to related neurodengenerative diseases is also provided. Methods of the invention also provide protection for patients undergoing cytotoxic therapy from side effects such as gastrointestinal (GI) mucositis.

12 Claims, 4 Drawing Sheets

*TGFα*

```
                         SEQUENCE LISTING

<160> NUMBER OF SEQ ID NOS: 6

<210> SEQ ID NO 1
<211> LENGTH: 50
<212> TYPE: PRT
<213> ORGANISM: Homo sapiens

<400> SEQUENCE: 1

Val Val Ser His Phe Asn Asp Cys Pro Asp Ser His Thr Gln Phe Cys
1               5                   10                  15

Phe His Gly Thr Cys Arg Phe Leu Val Gln Glu Asp Lys Pro Ala Cys
            20                  25                  30

Val Cys His Ser Gly Tyr Val Gly Ala Arg Cys Glu His Ala Asp Leu
        35                  40                  45

Leu Ala
    50

<210> SEQ ID NO 2
<211> LENGTH: 50
<212> TYPE: PRT
<213> ORGANISM: Rattus norvegicus

<400> SEQUENCE: 2

Val Val Ser His Phe Asn Lys Cys Pro Asp Ser His Thr Gln Tyr Cys
1               5                   10                  15

Phe His Gly Thr Cys Arg Phe Leu Val Gln Glu Glu Lys Pro Ala Cys
            20                  25                  30

Val Cys His Ser Gly Tyr Val Gly Val Arg Cys Glu His Ala Asp Leu
        35                  40                  45

Asp Ala
    50

<210> SEQ ID NO 3
<211> LENGTH: 57
<212> TYPE: PRT
<213> ORGANISM: Artificial Sequence
<220> FEATURE:
<223> OTHER INFORMATION: Description of Artificial Sequence: A modified
      human TGF-alpha sequence

<400> SEQUENCE: 3

Ser Leu Ser Leu Pro Ala Met Val Val Ser His Phe Asn Asp Cys Pro
1               5                   10                  15
```

```
-continued

Asp Ser His Thr Gln Phe Cys Phe His Gly Thr Cys Arg Phe Leu Val
            20                  25                  30

Gln Glu Asp Lys Pro Ala Cys Val Cys His Ser Gly Tyr Val Gly Ala
        35                  40                  45

Arg Cys Glu His Ala Asp Leu Leu Ala
    50                  55

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: An
      artificial peptide sequence
<220> FEATURE:
<221> NAME/KEY: UNSURE
<222> LOCATION: ()
<223> OTHER INFORMATION: X at residue 1, 5, 7 to 9 are independently
      V G or A; X at residue 6 is Y or F; and X at residue 10
      is R or K.

<400> SEQUENCE: 4

Xaa Cys His Ser Xaa Xaa Xaa Xaa Xaa Xaa Cys
 1               5                      10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Artificial
      peptide sequence
<220> FEATURE:
<221> NAME/KEY: UNSURE
<222> LOCATION: (1)..(7)
<223> OTHER INFORMATION: X at residue 1 and 4 are E or D; X at residue 3
      and 7 are V, G, or A; X at residue 5 is L or I;
      and X at residue 6 is D or E.

<400> SEQUENCE: 5

Xaa His Xaa Xaa Xaa Xaa Xaa
 1               5

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Artificial
      Peptide Sequence
<220> FEATURE:
<221> NAME/KEY: UNSURE
<222> LOCATION: (1)..(18)
<223> OTHER INFORMATION: X at residues 1, 5, 7-9, 14, 18 are indep.
      V, G or A; X at residues 6 is Y or F; X at residue 10 is R
      or K; X at residue 12, 15 is indep. E or D; X at
      residue 16 is L or I; X at residue 17 is D or E

<400> SEQUENCE: 6

Xaa Cys His Ser Xaa Xaa Xaa Xaa Xaa Cys Xaa His Xaa Xaa Xaa
 1               5                  10                  15

Xaa Xaa
```

METHODS OF INCREASING BODY WEIGHT IN A SUBJECT BY ADMINISTERING TGF-α

CROSS REFERENCE TO RELATED APPLICATIONS

This application is a continuation-in-part of U.S. application Ser. No. 09/459,813, filed Dec. 13, 1999, which is a continuation-in-part of U.S. application Ser. No. 09/299,473, filed Apr. 26, 1999, the disclosures of which are herein incorporated by reference in their entirety.

FIELD OF THE INVENTION

The invention relates generally to transforming growth factor alpha ( ) and more specifically to methods of using TGF-α for stimulating hematopoiesis, for suppressing immune function associated with autoimmune diseases, for suppressing inflammatory responses mediated by excessive histamine release and by expression of TNF-receptors and associated pro-inflammatory cytokines, and for treating cachexia or for treating or preventing mucositis and gastrointestinal-associated disorders.

BACKGROUND

There are several disease treatments that could significantly benefit by having cells regenerate after injury or lesion formation, particularly in the CNS, in the immune system and in the gastrointestinal tract. In some instances, a particular treatment for a disease often detrimentally affects the subject being treated. For example, administration of chemotherapeutic agents to subjects results in destruction of healthy cells, for example, cells of the gastrointestinal tract. A number treatment-related disorders are related to the choice of chemotherapeutic agent. Such agents include carmustine (BCNU), chlorambucil (LEUKERAN), cisplatin (PLATINOL), Cytarabine, doxorubicin (ADRIAMYCIN), fluorouracil (5-FU), methoxetrate (MEXATE), taxol, CPT111, etoposide, and plicamycin (MITHRACIN) which are known for their direct stomatotoxic potential (Sonis, 1993, "Oral Complications in Cancer Therapy," In: Principles and Practice of Oncology, pp. 2385–2394, DeVitta et al., Eds., J. B. Lippincott, Philadelphia) and hence incidence of mucositis.

Oral mucositis can be initiated by the cytotoxic effects of chemotherapy and/or radiotherapy on the rapidly dividing epithelial cells of the oropharyngeal mucosa, and is exacerbated by infection with both endogenous oral flora and opportunistic bacterial and fungal pathogens. Complications related to oral mucositis vary in the different patient populations affected, but typically include pain, poor oral intake with consequent dehydration and weight loss, and systemic infection with organisms originating in the oral cavity. The pain associated with oral mucositis may be severe requiring narcotic analgesics, and the difficulty in eating can result in patients receiving total parenteral nutrition.

Current therapies have been directed at decreasing oral flora and the extent of infection of oral ulcerations. Systemic treatment with G- and GM-CSF has been shown to result in a decreased incidence of oral mucositis, presumably by allowing for more rapid neutrophil recovery and thus an improved ability to combat infection, although it has been postulated that the CSFs may have a more direct effect on the oral mucosa (Chi et al., 1995, J. Clin. Oncol. 13:2620–2628). In one study, GM-CSF was reported to exacerbate mucositis. (Cartee et al., 1994, Cytokine 7:471–477). Benzydamine hydrochloride, a nonsteroidal drug with analgesic and antimicrobial properties, has been studied both in patients undergoing radiation therapy and in patients receiving intra-arterial chemotherapy.

In addition, diseases associated with epithelial cell depletion in the gastrointestinal tract often increase the risk of related disorders. Such related disorders include infection by opportunistic pathogens as well as weight loss associated with the loss in nutrient uptake in the gastrointestinal tract.

SUMMARY OF THE INVENTION

The present invention is based on the seminal discovery that TGF-α and functionally related polypeptides, TGF-α mimetics, functional TGF-α peptides, and polynucleotides encoding such polypeptides and peptide fragments are effective for treating or preventing weight-loss in subjects having disorders or diseases associated with weight-loss (e.g., cachexia). In addition, the polypeptides of the invention have mitogenic and barrier function (e.g., protective) effects on stem cells and their differentiated progeny from a variety of tissues including the gastrointestinal system, the nervous system and the hematopoietic system.

In a first embodiment, the invention provides a method of treating a subject having or at risk of having cachexia comprising administering to the subject a transforming growth factor-alpha (TGF-α) polypeptide in an amount effective to prevent or reduce weight-loss. In one aspect, the invention provides a method of increasing the body weight of a subject comprising administering to the subject, prior to, simultaneously with, or substantially following chemotherapy, a transforming growth factor-alpha (TGF-α) polypeptide in an amount effective to increase the weight of the subject. In one aspect the subject has AIDS related complex (ARC) or AIDS and cachexia associated with such diseases.

In another embodiment, the invention provides a method for treating or preventing mucositis of the gastrointestinal tract in a subject, comprising administering a TGFα or related polypeptide in an amount effective to treat or prevent mucositis in the subject. For example, a subject undergoing chemotherapy can be treated by the method of the invention.

The invention also provides a polypeptide comprising a peptide having a sequence $NH_2$-$X_{1a}$-Cys-His-Ser-$X_{1b}$-$X_2$-$X_{1a}$-$X_{1b}$-$X_{1a}$-$X_3$-Cys-COOH (SEQ ID NO:4) wherein $X_{1a}$ and $X_{1b}$ are independently Val, Gly or Ala; $X_2$ is Tyr or Phe; $X_3$ is Arg or Lys; and the two Cys moieties are linked via a disulfide bond to form an at least 11-amino acid functional peptide having TGF-α activity.

In another embodiment, the invention provides a polypeptide comprising a peptide having a sequence $NH_2$-$X_{1a}$-Cys-His-Ser-$X_{1b}$-$X_2$-$X_{1a}$-$X_{1b}$-$X_{1a}$-$X_3$-Cys-COOH (SEQ ID NO:4) wherein $X_{1a}$ and $X_{1b}$ are independently Val, Gly or Ala; $X_2$ is Tyr or Phe; $X_3$ is Arg or Lys; and the two Cys moieties are linked via a disulfide bond to form an at least 11-amino acid functional peptide having TGF-α activity and wherein at least one or more of the following amino acids are linked to the C-terminal Cys moiety of SEQ ID NO:4: -$X_4$-His-$X_{1c}$-$X_4$-$X_5$-$X_6$-$X_{1c}$ (SEQ ID NO:5) wherein $X_4$ is Glu or Asp; $X_5$ is Leu or Ile; and $X_6$ is Asp or Glu.

In yet another embodiment, the invention provides a pharmaceutical composition comprising a polypeptide having a sequence $NH_2$-$X_{1a}$-Cys-His-Ser-$X_{1b}$-$X_2$-$X_{1a}$-$X_{1b}$-$X_{1a}$-$X_3$-Cys COOH (SEQ ID NO:4) wherein $X_{1a}$ and $X_{1b}$ are independently Val, Gly or Ala; $X_2$ is Tyr or Phe; $X_3$ is Arg or Lys; and the two Cys moieties are linked via a disulfide bond to form an at least 11-amino acid functional peptide having TGF-α activity, and a pharmaceutically acceptable carrier. In addition, at least one or more of the following amino acids are linked to the C-terminal Cys moiety of SEQ ID NO:4: -$X_4$-His-$X_{1c}$-$X_4$-$X_5$-$X_6$-$X_{1c}$ (SEQ ID NO:5) wherein $X_4$ is Glu or Asp; $X_5$ is Leu or Ile; and $X_6$ is Asp or Glu.

The invention also provides a compound that acts as a TGF-α mimetic, comprising a compound of formula: loop peptide N-terminus-linker-cyclic $C_4H_8N_2$-linker-loop peptide N-terminus wherein the linker moiety is designed to link the N-terminus of the loop peptide to a nitrogen atom of the ring $C_4H_8N_2$ and wherein the loop peptide has a sequence $NH_2$-$X_{1a}$-Cys-His-Ser-$X_{1b}$-$X_2$-$X_{1a}$-$X_{1b}$-$X_{1a}$-$X_3$-Cys COOH (SEQ ID NO:4) wherein $X_{1a}$ and $X_{1b}$ are independently Val, Gly or Ala; $X_2$ is Tyr or Phe; $X_3$ is Arg or Lys; and the two Cys moieties are linked via a disulfide bond to form an at least 11-amino acid functional peptide having TGF-α activity.

DETAILED DESCRIPTION OF THE INVENTION

The present invention provides compositions of TGF-α polypeptides, TGF-α mimetics, TGF-α related polypeptides and functional fragments thereof as well as polynucleotides encoding the polypeptides and fragments thereof In addition, the invention provides methods of using the polypeptides and polynucleotides of the invention for treating or preventing a number of diseases and disorders.

Transforming Growth Factor-α

TGF-α is a member of the epidermal growth factor (EGF) family and interacts with one or more receptors in the EGF-family of receptors. TGF-α stimulates the receptor's endogenous tyrosine kinase activity which results in activating various cellular functions, such as stimulating a mitogenic or migration response in a wide variety of cell types. TGF-α and EGF mRNAs reach their highest levels and relative abundance (compared to total RNA) in the early postnatal period and decrease thereafter, suggesting a role in embryonic development. From a histological perspective, TGF-α is found in numerous cell types and tissues throughout the body. The active form of TGF-α is derived from a larger 30–35 kD precursor and contains 50 amino acids. Human TGF-α shares only a 30% structural homology with the 53-amino acid form of EGF, but includes conservation and spacing of all six cysteine residues. TGFα is highly conserved among species. For example, the rat and human polypeptides share about 90% homology compared to a 70% homology as between the rat and human EGF polypeptide. The amino acid sequence of human TGFα is shown in SEQ ID NO:1. TGFα shares cysteine disulfide bond structures with a family of proteins including vaccinia growth factor, amphiregulin precursor, betacellulin precursor, heparin binding EGF-like growth factor, epiregulin (rodent only), HUS 19878, myxomavirus growth factor (MGF), Shope fibroma virus growth factor (SFGF), and schwannoma derived growth factor. Such TGF-α related polypeptides are also useful in the methods of the invention.

TGF-α is an acid and heat stable polypeptide of about 5.6 kDa molecular weight. It is synthesized as a larger 30–35 kDa molecular weight glycosylated and membrane-bound precursor protein wherein the soluble 5.6 kDa active form is released following specific cleavage by an elastase-like protease. TGF-α binds with high affinity in the nanomolar range and induces autophosphorylation of one or more members of EGF receptor family (e.g., ErbB1 through 4) to transduce subsequent signal pathways with the EGF receptors. TGF-α is 50 amino acids in length and has three disulfide bonds to form its tertiary configuration. All three disulfide bonds are required for activity. TGF-α is stored in precursor form in alpha granules of some secretory cells. Moreover, the primary amino acid sequence is highly conserved among various species examined, such as more than 92% homology at the amino acid level as between human and rat TGFα polypeptides.

Figure 1:
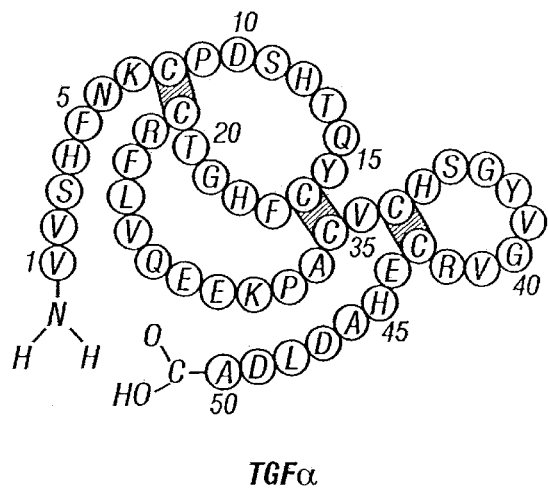
FIG. 1 shows the structure of rat TGFα polypeptide and its 50 amino acids arranged into three loops (SEQ ID NO:2). The human TGFα sequence is provided in SEQ ID NO:1 with a similar tertiary structure and a close sequence homology.

Human TGFα is a polypeptide of 50 amino acids. The corresponding rat sequence is shown in FIG. 1. The human or rat TGFα polypeptide can be divided roughly into three loop regions corresponding roughly (starting at the N terminus) to amino acids 1–21, to amino acids 16–32, and to amino acids 33–50. As discussed more fully below, the invention provides functional fragments of TGF-α that retain TGF-α biological activity. "Functional fragment" as used herein means a TGF-α peptide that is a fragment or a modified fragment of a full length TGF-α polypeptide or related polypeptide so long as the fragment retains some TGF-α related biological activity (e.g., interacts with an EGF family receptor, stimulates proliferation or migration of stem cells, useful for treating or preventing cachexia). Other biological activities associated with the polypeptides of the invention include, for example, mitogenic effects on stem cells and their more differentiated progeny of various tissues (e.g., epithelial stem cells, hematopoietic stem cells, neural stem cells, liver stem cells, keratinocyte stem cells, and pancreatic derived stem cells).

The mucosal epithelium of the intestine is in a continually dynamic state known as "epithelial renewal" in which undifferentiated stem cells from a proliferative crypt zone divide, differentiate and migrate to the luminal surface. Once terminally differentiated, mucosal epithelial cells are sloughed from the tips of the villi. The turnover of the crypt-villus cell population is rapid and occurs every 24–72 hours. Continuous exfoliation of the cells at the villus tip is counterbalanced by ongoing proliferation in the crypt so that net intestinal epithelial mass remains relatively constant. The rapidly-proliferating epithelium of the gastrointestinal tract is extremely sensitive to cytotoxic drugs that are widely used in cancer chemotherapy. By "gastrointestinal tract" is meant, for example, the tissues of the mouth, esophagus, stomach, small intestine, large intestine, rectum and anus. This "side effect" reduces the tolerated dose of such drugs as it can cause a breakdown of the GI barrier function and septic propagate a septic condition in a patient already immuno-compromised. This can also lead to life-threatening hemorrhage. Therefore, there is a need in the art for the development of products and delivery systems that stimulate the repair and rejuvenation of mucosal epithelium in the gastrointestinal tract to provide benefit to subjects having, for example, weight-loss disorders associated with chemotherapy and radiation therapy for cancer as well as disorders or diseases associated with pathogens such as HIV.

Accordingly, the invention provides a class of peptides, including TGF-α and those smaller than the 50 amino acid human TGF-α, yet retaining TGF-α biological activity, which are useful as pharmacologic and therapeutic agents. Other polypeptides or fragments thereof include TGF-related polypeptides that have the biological activity of TGF-α (e.g., amphiregulin, vaccinia growth factor, myxomavirus growth factor (MGF), Shope fibroma virus growth factor (SFGF), heparin-binding EGF-like growth factor (HB-EGF)).

The invention also provides methods of using TGF-α, related polypeptides and peptide fragments thereof as disclosed herein to stimulate hematopoiesis in subjects undergoing cytotoxic cancer chemotherapy and to act as a cytoprotective agents and in treatments for subjects at risk of or having weight-loss disorders associated with cancer cytotoxic therapy. Such disorders include for example, gastrointestinal (GI) mucositis, which can be the result of cytotoxic therapy. While not wanting to be bound to a particular theory, it is believed TGF-α may alleviate GI mucositis, in part, through its mitogenic actvity for GI epithelial stem cells.

TGFα has been investigated extensively and has recently been identified as useful for treating subjects with neurological deficits. This mechanism is thought to stimulate proliferation and migration of stem cells of neural origin to those sites or lesions in a deficit. For example, Parkinson's Disease is characterized by resting tremor, rigidity, inability to initiate movement (akinesia) and slowness of movement (bradykinesia). The motor deficits are associated with progressive degeneration of the dopaminergic innervation to the nucleus accumbens and degeneration of noradrenergic cells of the locus ceruleus and serotonergic neurons of the raphe. Up to 80% of nigral dopamine neurons can be lost before significant motor deficits are manifest. TGFα was shown, when infused into rat brains, to be useful for the treatment of neurodegenerative disorders. Intracerebroventricular (ICV) or intrastriatal infusions of TGFα induced neuronal stem cell proliferation, but degenerating or damaged or otherwise abnormal cells needed to be present to facilitate migration of the neuronal stem cells to a site of injury on a scale sufficient to impact recovery from an associated neurological deficit. Forebrain neural stem cells, that give rise to migrating progenitor cells that affect treatment and recovery from a neurological deficit disorder, are the migrating cells that affect treatment recovery from a neural deficit disorder (e.g., Parkinson's Disease, Huntington's Disease, Alzheimer's Disease and the like).

Neural stem cells have been found in subependyma throughout the adult rodent CNS (Ray et al. Soc. *Neurosci.* 22:394.5, 1996) and in the subependyma of adult human forebrain (Kirschenbaum et al., *Cerebral Cortex* 4:576–589, 1994). Thus, the discovery that TGFα stimulates proliferation of neural stem cells and promotes migration to a site of injury or deficit has led to its investigation for the treatment of a neurodegenerative disorder (Alzheimer's Disease, Huntington's Disease and Parkinson's Disease) or CNS traumatic injury (e.g., spinal chord injury), demyelinating disease, CNS inflammatory disease, CNS autoimmune disease (e.g., multiple sclerosis) and CNS ischemic disease (e.g., stroke or brain attack).

A CNS stem cell has the potential to differentiate into neurons and astrocytes as well as self replication and thus self renewal. Both neuronal and glial cells are derived from a common precursor cell. In the vertebrate CNS, pluripotential cells have been identified in vitro and in vivo. Certain mitogens, such as TGF-α, can cause proliferation of CNS pluripotential cells in vitro. Thus, it is possible to harvest such cell from a subject, treat them ex vivo to stimulate proliferation in culture and then readminister the cells back to a subject. Immunohistochemical analysis in the human brain supports the notion that TGF-α and its 35 kD precursor are widely distributed in neurons and glial cells both during development and during adulthood. In TGF-α knockout mice genetically altered to lack expression of functioning TGF-α, there was a decrease in neural progenitor cell proliferation in forebrain subependyma, providing evidence for TGF-α as a proliferative factor for neural progenitor cells.

TGF-α is found mainly in various neurons of the CNS during development and in the adult brain in the cerebral neocortex, hippocampus and striatum. It is also found in glial cells, primarily in the cerebral and cerebellar cortex areas. Northern blot analyses showed that TGFα but not EGF (epidermal growth factor) is the most abundant ligand that binds to one or more of the EGF receptor family in the brain. TGFα mRNA levels were 15–170 times higher than EGF in cerebellum and cerebral cortex. TGFα also appears in germinal centers of the brain during neurogenesis and gliogenesis in the developing brain. In the midbrain, the distribution of TGFα overlaps with tyrosine hydroxylase mRNA and fetal dopaminergic neurons. In culture, TGFα enhanced survival and neurite outgrowth of neonatal rat dorsal ganglion neurons (EGF did not) and survival and differentiation of CNS neurons. TGFα induced proliferation of neural precursor cells of the murine embryonic mesencephalon and further induced a significant increase in the number of astroglia and microglia in fetal rat medial septal cells. TGFα increased glutamic acid decarboxylase activity and decreased choline actetyltransferase activity. Thus, TGFα acted as a general neuronal survival factor affecting both cholinergic and GABAergic neurons. In addition, TGFα is a mitogen for pluripotent brain stem cells. Forebrain subependyma contains nestin positive neural stem cells and their progeny, which are constitutively proliferating progenitor epithelial cells. A "knockout" mouse that was genetically engineered to delete the gene for TGFα showed a reduction in neuronal progenitor cells in the subependyma and a reduction in neuronal progenitors that migrate to the olifactory bulb. In vitro, TGFα promoted dopamine uptake in fetal rat dopaminergic neurons in a dose-dependent and time-dependent manner. TGFα selectively promoted dopaminergic cell survival, enhanced neurite length, branch number and the soma area of tyrosine hydroxylase immunopositive cells. The levels of TGFα were elevated in ventricular cerebrospinal fluid in juvenile parkinsonism and Parkinson's Disease and may represent a compensatory response to neurodegeneration. Further, TGFα prevented a striatal neuronal degeneration in an animal model of Huntington's Disease.

Nucleic Acids and Vectors

Polynucleotide or nucleic acid sequence refers to a polymeric form of nucleotides. In some instances a polynucleotide refers to a sequence that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. in addition, the polynucleotide sequence involved in producing a polypeptide chain can include regions preceding and following the coding region (leader and trailer) as well as intervening sequences (introns) between individual coding segments (exons) depending upon the source of the polynucleotide sequence.

The term polynucleotide(s) generally refers to any polyribonucleotide or polydeoxyribonucleotide, which may be unmodified RNA or DNA or modified RNA or DNA. Thus, for instance, polynucleotides as used herein refers to, among others, single-and double-stranded DNA, DNA that is a mixture of single-and double-stranded regions, single-and double-stranded RNA, and RNA that is mixture of single- and double-stranded regions, hybrid molecules comprising DNA and RNA that may be single-stranded or, more typically, double-stranded or a mixture of single-and double-stranded regions.

In addition, the polynucleotides or nucleic acid sequences may contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

Nucleic acid sequences can be created which encode a fusion protein (e.g., a TGF-α polypeptide and another polypeptide, such as a targeting sequence) and can be operatively linked to expression control sequences. "Operatively linked" refers to a juxtaposition wherein the components so described are in a relationship permitting them to function in their intended manner. For example, a coding sequence is "operably linked" to another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the of a polynucleotide sequence. Both constitutive and inducible promoters, are included in the invention (see e.g., Bitter et al., Methods in Enzymology 153:516–544, 1987). For example, when cloning in bacterial systems, inducible promoters such as pL of bacteriophage, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

A nucleic acid sequence of the invention including, for example, a polynucleotide encoding a fusion protein, may be inserted into a recombinant expression vector. A recombinant expression vector generally refers to a plasmid, virus or other vehicle known in the art that has been manipulated by insertion or incorporation of a nucleic acid sequences. For example, a recombinant expression vector of the invention includes a polynucleotide sequence encoding a TGF-α polypeptide having a sequence as set forth in SEQ ID NO:1, 2, 3, 4 or 6 or fragment thereof (as described more fully below). The expression vector typically contains an origin of replication, a promoter, as well as specific genes which allow phenotypic selection of the transformed cells. Vectors suitable for use in the invention include, but are not limited to the T7-based expression vector for expression in bacteria (Rosenberg, et al., Gene 56:125, 1987), the pMSXND expression vector for expression in mammalian cells (Lee and Nathans, J. Biol. Chem. 263:3521, 1988), baculovirus-derived vectors for expression in insect cells, cauliflower mosaic virus, CaMV; tobacco mosaic virus, TMV. The nucleic acid sequences of the invention can also include a localization sequence to direct the indicator to particular cellular sites by fusion to appropriate organellar targeting signals or localized host proteins. For example, a polynucleotide encoding a localization sequence, or signal sequence, can be used as a repressor and thus can be ligated or fused at the 5' terminus of a polynucleotide encoding a polypeptide or a polypeptide fragment of the invention such that the localization or signal peptide is located at the amino terminal end of a resulting polypeptide. The construction of expression vectors and the expression of genes in transfected cells involves the use of molecular cloning techniques also well known in the art. (See, for example, Sambrook et al., Molecular Cloning—A Laboratory Manual, Cold Spring Harbor Laboratory, Cold Spring Harbor, N.Y., 1989, and Current Protocols in Molecular Biology, M. Ausubel et al., eds., (Current Protocols, a joint venture between Greene Publishing Associates, Inc. and John Wiley & Sons, Inc., most recent Supplement)). These methods include in vitro recombinant DNA techniques, synthetic techniques and in vivo recombination/genetic recombination. (See also, Maniatis, et al., Molecular Cloning A Laboratory Manual, Cold Spring Harbor Laboratory, N.Y., 1989).

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., "Expression and Secretion Vectors for Yeast," in Methods in Enzymology, Eds. Wu & Grossman, 1987, Acad. Press, N.Y., Vol. 153, pp.516–544, 1987; Glover, DNA Cloning, Vol. II, IRL Press, Wash., D.C., Ch. 3, 1986; and Bitter, "Heterologous Gene Expression in Yeast," Methods in Enzymology, Eds. Berger & Kimmel, Acad. Press, N.Y., Vol. 152, pp. 673–684, 1987; and The Molecular Biology of the Yeast Saccharomyces, Eds. Strathern et al., Cold Spring Harbor Press, Vols. I and II, 1982. A constitutive yeast promoter such as ADH or LEU2 or an inducible promoter such as GAL may be used ("Cloning in Yeast," Ch. 3, R. Rothstein In: DNA Cloning Vol.11, A Practical Approach, Ed. DM Glover, IRL Press, Wash., D.C., 1986). Alternatively, vectors may be used which promote integration of foreign DNA sequences into the yeast chromosome.

An alternative expression system which could be used to express a TGF-α polypeptide or function fragment of the invention is an insect system. In one such system, *Autographa californica* nuclear polyhedrosis virus (AcNPV) is used as a vector to express foreign or mutated polynucleotide sequences. The virus grows in *Spodoptera frugiperda* cells. The sequence encoding a polypeptide of the invention may be cloned into non-essential regions (for example, the polyhedrin gene) of the virus and placed under control of an AcNPV promoter (for example the polyhedrin promoter). Successful insertion of the sequences coding for a polypeptide of the invention will result in inactivation of the polyhedrin gene and production of non-occluded recombinant virus (i.e., virus lacking the proteinaceous coat coded for by the polyhedrin gene). These recombinant viruses are then used to infect *S. frugiperda* cells in which the inserted gene is expressed, see Smith, et al., J. Viol. 46:584, 1983; Smith, U.S. Pat. No. 4,215,051.

The vectors of the invention can be used to transform a host cell. By transform or transformation is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell.

A transformed cell or host cell generally refers to a cell (e.g., prokaryotic or eukaryotic) into which (or into an ancestor of which) has been introduced, by means of recombinant DNA techniques, a polynucleotide molecule encoding a TGF-α polypeptide or functional fragments thereof (e.g., a functional fragment as set forth in SEQ ID NO:4, as described below).

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, methods of transfection or transformation with DNA include calcium phosphate co-precipitates, conventional mechanical procedures such as microinjection, electroporation, insertion of a plasmid encased in liposomes, or virus vectors, as well as others known in the art, may be used. Eukaryotic cells can also be cotransfected with DNA sequences encoding a TGF-α polypeptide or fragment and a second foreign DNA molecule encoding a selectable marker, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Typically, a eukaryotic host will be utilized as the host cell. The eukaryotic cell may be a yeast cell (e.g., *Saccharomyces cerevisiae*), an insect cell (e.g., Drosophila sp.) or may be a mammalian cell, including a human cell.

Eukaryotic systems, and mammalian expression systems, allow for post-translational modifications of expressed mammalian proteins to occur. Eukaryotic cells which possess the cellular machinery for processing of the primary transcript, glycosylation, phosphorylation, and, advantageously secretion of the gene product should be used. Such host cell lines may include, but are not limited to, CHO, VERO, BHK, HeLa, COS, MDCK, Jurkat, HEK-293, and WI38.

Mammalian cell systems which utilize recombinant viruses or viral elements to direct expression maybe engineered. For example, when using adenovirus expression vectors, a polynucleotide encoding a TGF-α polypeptide or fragment thereof may be ligated to an adenovirus transcription/ translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a TGF-α polypeptide or fragment thereof in infected hosts (e.g., see Logan & Shenk, Proc. Natl. Acad. Sci. USA, 81:3655–3659, 1984). Alternatively, the vaccinia virus 7.5K promoter may be. used. (e.g., see, Mackett, et al., Proc. Natl. Acad. Sci. USA, 79:7415–7419, 1982; Mackett, et al., J. Virol. 49:857–864, 1984; Panicali, et al., Proc. Natl. Acad. Sci. USA 79:4927–4931, 1982). Of particular interest are vectors based on bovine papilloma virus which have the ability to replicate as extrachromosomal elements (Sarver, et al., Mol. Cell. Biol. 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the cDNA encoding a TGF-α polypeptide or functional fragment controlled by appropriate expression control elements (e.g. promoter, enhancer, sequences, transcription terminators, polyadenylation sites, etc.), and a selectable marker. The selectable marker in the recombinant vector confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including, but not limited to, the herpes simplex virus thymidine kinase (Wigler, et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817, 1980) genes can be employed in tk-, hgprt- or aprt- cells respectively. Also, anti-metabolite resistance can be used as the basis of selection for dhfr, which confers resistance to methotrexate (Wigler, et al, Proc. Natl. Acad. Sci. USA, 77:3567, 1980; O'Hare, et al., Proc. Natl. Acad. Sci. USA, 8:1527, 1981); gpt, which confers resistance to mycophenolic acid (Mulligan & Berg, Proc. Natl. Acad. Sci. USA, 78:2072, 1981); neo, which confers resistance to the aminoglycoside G-418 (Colberre-Garapin, et al., J. Mol. Biol. 150:1, 1981); and hygro, which confers resistance to hygromycin (Santerre, et al, Gene 30:147, 1984) genes. Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA 85:8047, 1988); and ODC (ornithine decarboxylase) which confers resistance to the ornithine decarboxylase inhibitor, 2-(difluoromethyl)-DL-omithine, DFMO (McConlogue L., In: Current Communications in Molecular Biology, Cold Spring Harbor Laboratory, ed., 1987).

The term "primer" as used herein refers to an oligonucleotide, whether natural or synthetic, which is capable of acting as a point of initiation of synthesis when placed under conditions in which primer extension is initiated or possible. Synthesis of a primer extension product which is complementary to a nucleic acid strand is initiated in the presence of nucleoside triphosphates and a polymerase in an appropriate buffer at a suitable temperature.

Proteins and Polypeptides

A polypeptide or protein refers to a polymer in which the monomers are amino acid residues which are joined together through amide bonds. When the amino acids are alpha-amino acids, either the L-optical isomer or the D-optical isomer can be used, the L-isomers being typical. A TGF-α polypeptide or TGF-α related polypeptide is intended to encompass an amino acid sequence, including modified sequences such as glycoproteins, which exhibit TGF-α activity. The polypeptides of the invention encompass amino acid sequences of human TGF-α as shown in SEQ ID NO:1 as well as polypeptides that have structural and/or functional characteristics of TGF-α. For example, a polypeptide or a TGF-α related polypeptide of the invention may include a polypeptide that shares a cysteine disulfide bond structure similar to TGF-α such as a related family of proteins including vaccinia growth factor, amphiregulin precursor, betacellulin precursor, heparin binding EGF-like growth factor, epiregulin (rodent only), HUS 19878, myxomavirus growth factor (MGF), Shope fibroma virus growth factor (SFGF), and schwannoma derived growth factor. In addition, a polypeptide of the invention will have one or more functional characteristics related to TGF-α including, for example, the ability to interact with an EGF family receptor member, stimulate proliferation or migration of stem cells, or to treat or prevent cachexia.

The polypeptides of the invention are intended to cover naturally occurring proteins, as well as those which are recombinantly or synthetically synthesized. In addition, a TGF-α or related polypeptide can occur in at least two different conformations wherein both conformations have the same or substantially the same amino acid sequence but have different three dimensional structures so long as the have a biological activity related to TGF-α. Polypeptide or protein fragments of TGF-α are also encompassed by the invention such as those described by formulas I, II, and III (see below). Fragments can have the same or substantially the same amino acid sequence as the naturally occurring protein. A polypeptide or peptide having substantially the same sequence means that an amino acid sequence is largely, but not entirely, the same, but retains a functional activity of the sequence to which it is related. In general polypeptides of the present invention include peptides, or full length protein, that contains substitutions, deletions, or insertions into the protein backbone, that would still have an approximately 50%–70% homology to the original protein over the corresponding portion. A yet greater degree of departure from homology is allowed if like-amino acids, i.e. conservative amino acid substitutions, do not count as a change in the sequence. Polypeptide fragments of the invention retain a biological activity associated with TGF-α as described above.

Homology to TGF-α polypeptide can be measured using standard sequence analysis software (e.g., Sequence Analysis Software Package of the Genetics Computer Group, University of Wisconsin Biotechnology Center, 1710 University Avenue, Madison, Wis. 53705; also see Ausubel, et al., supra). Such procedures and algorithms include, for example, a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF.

A polypeptide may be substantially related but for a conservative variation, such polypeptides being encompassed by the invention. A conservative variation denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. Other illustrative examples of conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine. The term "conservative variation" also includes the use of a substituted amino acid in place of an unsubstituted parent amino acid provided that antibodies raised to the substituted polypeptide also immunoreact with the unsubstituted polypeptide.

Modifications and substitutions are not limited to replacement of amino acids. For a variety of purposes, such as increased stability, solubility, or configuration concerns, one skilled in the art will recognize the need to introduce, (by deletion, replacement, or addition) other modifications. Examples of such other modifications include incorporation of rare amino acids, dextra-amino acids, glycosylation sites, cytosine for specific disulfide bridge formation. The modified peptides can be chemically synthesized, or the isolated gene can be site-directed mutagenized, or a synthetic gene can be synthesized and expressed in bacteria, yeast, baculovirus, tissue culture and so on.

Solid-phase chemical peptide synthesis methods can also be used to synthesize the polypeptide or fragments of the invention. Such method have been known in the art since the early 1960's (Merrifield, R. B., *J. Am. Chem. Soc.*, 85, 2149–2154 (1963) (See also Stewart, J. M. and Young, J. D., Solid Phase Peptide Synthesis, 2 ed., Pierce Chemical Co., Rockford, Ill., pp. 11–12)) and have recently been employed in commercially available laboratory peptide design and synthesis kits (Cambridge Research Biochemicals). Such commercially available laboratory kits have generally utilized the teachings of H. M. Geysen et al, *Proc. Natl. Acad. Sci., USA*, 81, 3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. For example, if the peptide is from formula I or formula II (see below), a preferred means for synthesizing peptides of 10–18 amino acids in length is by direct peptide synthesis generally starting with the N-terminal amino acid and adding amino acids in the C terminal direction. TGFα has been made using recombinant techniques and is available as a laboratory reagent commercially. The bifunctional compounds of formula III are best synthesized with each loop peptide moiety synthesized and then added to the heterocyclic nitrogen atom using standard heterocyclic addition synthesis.

TGF-α Peptide Mimics

The functional peptides of the invention are based upon the discovery that a loop peptide of TGF-α exhibits TGF-α biological activity and can therefore stimulate CNS multipotent precursor cells to divide and migrate through the brain. This activity indicates that the loop peptide is effective to treat neurological deficits caused by a wide variety of diseases and injuries that each result in a neurological deficit in some specific area of the brain or specific kind of neuron. These include degenerative diseases, including the more common Alzheimer's Disease (AD), Parkinson's Disease (PD), and Huntington's Disease (HD), and the less common Pick's disease, progressive supranuclear palsy, striatonigral degeneration, cortico-basal degeneration, olivopontocerebellar atrophy, Leigh's disease, infantile necrotizing encephalomyelopathy, Hunter's disease, mucopolysaccharidosis, various leukodystrophies (such as Krabbe's disease, Pelizaeus-Merzbacher disease and the like), amaurotic (familial) idiocy, Kuf's disease, Spielmayer-Vogt disease, Tay Sachs disease, Batten disease, Jansky-Bielschowsky disease, Reye's disease, cerebral ataxia, chronic alcoholism, beriberi, Hallervorden-Spatz syndrome, cerebellar degeneration, and the like.

Further, injuries (traumatic or neurotoxic) that cause a loss of neuronal function can be treated by the functional peptides. Such injuries include, for example, gunshot wounds, injuries caused by blunt force, penetration injuries, injuries caused by surgical procedure (e.g., tumor removal, abscess removal, epilepsy lesion removal) poisoning (e.g., carbon monoxide), shaken baby syndrome, adverse reactions to medications, drug overdoses, and post-traumatic encephalopathy. Ischemia can further cause CNS injury due to disruption of blood flow or oxygen delivery that can kill or injure neurons and glial cells (e.g., TGF-α confers protection from ischemia in a porcine gastrointestinal model and a family member, Heparin-binding EGF, confers protection from ischemia in a rat stroke model). Such injuries can be treated by administration of the functional peptides and include, for example, injuries caused by stroke, anoxia, hypoxia, partial drowning, myoclonus, severe smoke inhalation, dystonias, and acquired hydrocephalus. Developmental disorders that can be treated by the functional peptides include, for example, schizophrenia, certain forms of severe mental retardation, cerebral palsey, congenital hydrocephalus, severe autism, Downs Syndrome, LHRH/hypothalamic disorder, and spina bifida. The functional peptides can be further used to treat disorders affecting vision caused by the loss or failure of retinal cells and include, for example, diabetic retinopathy, serious retinal detachment (associated with glaucoma), traumatic injury to the retina, retinal vascular occlusion, macular degeneration, optic nerve atrophy and other retinal degenerative diseases. Injuries to the spinal cord can be treated by the functional peptides. Examples of spinal cord injuries are post-polio syndrome, amyotrophic lateral sclerosis, traumatic injury, surgical injury, and paralytic diseases. Demylinating autoimmune disorders can be treated by administration of the functional peptides and include, for example, multiple sclerosis. Lastly, the functional peptides can be used to treat neurological deficits caused by infection of inflammatory diseases, including, for example, Creutzfeldt-Jacob disease and other slow virus infectious diseases of the CNS, AIDS encephalopathy, post-encephalitic Parkinsonism, viral encephalitis, bacterial meningitis and other CNS effects of infectious diseases.

By "functional" as used in connection with the peptides or peptide fragments of the invention is meant that the peptides or fragments have TGFα activity. This biological activity is associated with the peptides of formula I, formula II and formula III and the data available for TGFα.

Generally, the terms "treating", "treatment" and the like are used herein to mean affecting a subject, tissue or cell to obtain a desired pharmacologic and/or physiologic effect. The effect may be prophylactic in terms of completely or partially preventing a disease or disorder or sign or symptom thereof, and/or may be therapeutic in terms of a partial or complete cure for a disorder or disease and/or adverse effect attributable to the disorder or disease. "Treating" as used herein covers any treatment of, or prevention of, or inhibition of a disorder or disease in a subject. The subject can be an invertebrate, a vertebrate, a mammal, and particularly a human, and includes by way of example: (a) preventing the disease or disorder from occurring in a subject that may be predisposed to the disease or disorder, but has not yet been diagnosed as having it; (b) inhibiting the disease or disorder, i.e., arresting its progression; or (c) relieving or ameliorating the disease or disorder, i.e., causing regression.

The invention also provides methods of modulating weight-loss associated with disease and disorders of the gastrointestinal tract, for example, those associated with viral infections and chemotherapy by administering TGF-α or related polypeptides or fragments thereof which retain TGF-α biological activity (e.g., SEQ ID NO:1, 2, or 3, and the peptides of formula I, II, or III).

The invention provides a peptide having TGFα biological activity, comprising at least an 11-membered peptide compound of formula I (SEQ ID NO:4):

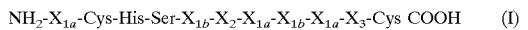
$$NH_2-X_{1a}-Cys-His-Ser-X_{1b}-X_2-X_{1a}-X_{1b}-X_{1a}-X_3-Cys\ COOH \quad (I)$$

wherein $X_1$ is independently Val, Gly or Ala, wherein $X_2$ is Tyr or Phe, wherein $X_3$ is Arg or Lys, and wherein the two Cys moieties form a disulfide bond to create an 11-amino acid functional peptide having a 10 member loop structure. In addition, at least one or more of the following amino acids of formula II (SEQ ID NO:5) may be added to the C terminus Cys moiety of formula I (SEQ ID NO:4):

$$-X_4-His-X_{1c}-X_4-X_5-X_6-X_{1c} \quad (II)$$

wherein $X_4$ is Glu or Asp, wherein $X_5$ is Leu or Ile, and wherein $X_6$ is Asp or Glu. Preferably, $X_{1a}$ is Val, $X_{1b}$ is Gly and $X_{1c}$ is Ala thereby producing an 11, 12, 13, 14, 15, 16, 17 or 18 amino acid peptide. Preferably, $X_2$ is Tyr, and $X_3$ is Arg. Accordingly, in one embodiment the functional peptide of the invention has a sequence:

$$NH_2-X_{1a}-Cys-His-Ser-X_{1b}-X_2-X_{1a}-X_{1b}-X_{1a}-X_3-Cys-X_4-His-X_{1c}-X_4-X_5-X_6-X_{1c}-COOH \quad (SEQ\ ID\ NO:6)$$

SEQ ID NO:6 forms a 10 member loop structure with a 7 member tail that can be varied in length. In addition, SEQ ID NO:6 can form dimers comprising, for example, a 34-mer peptide. Accordingly, the functional peptide can be from about 10 to 18 amino acids in length (e.g., 10, 11, 12, 13, 14, 15, 16, 17, or 18 amino acids) wherein $X_{1a}$ is Val, $X_{1b}$ is Gly, $X_{1c}$ is Ala and $X_4$ is Gly and may also comprise hetero-or homo-dimers of various TGF-α peptides described herein. Such dimers may have greater or reduced activities as compared to monomers.

The invention further provides a pharmaceutical composition comprising a peptide in a pharmaceutically acceptable carrier, wherein the peptide compound comprises at least about a 10 to 18-membered peptide compound of formula I (SEQ ID NO:4, including members of SEQ ID NO:5 attached to SEQ ID NO:4 and including SEQ ID NO:6). Preferably, at least one or more of the seven amino acids of formula II are added to the C terminus Cys moiety. Most preferably, the functional peptide is 18 amino acids in length wherein $X_{1a}$ is Val, $X_{1b}$ is Gly, $X_{1c}$ is Ala and $X_4$ is Gly. The peptides described herein are all useful in the methods of the invention.

The invention further provides a method for treating a neurodegenerative disease with a pharmaceutically active TGF-α polypeptide, functional fragment peptide thereof or a pharmaceutically active TGF-α57 polypeptide, wherein the peptide comprises at least an 11-membered peptide compound of formula I or a polypeptide of formula III, wherein formula I (SEQ ID NO:4) is:

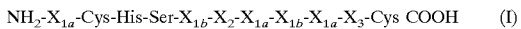
$$NH_2-X_{1a}-Cys-His-Ser-X_{1b}-X_2-X_{1a}-X_{1b}-X_{1a}-X_3-Cys\ COOH \quad (I)$$

wherein $X_1$ is independently Val, Gly or Ala, wherein $X_2$ is Try or Phe, wherein $X_3$ is Arg or Lys, and wherein the two Cys moieties form a disulfide bond to create an 11-amino acid functional peptide; and wherein formula III is:

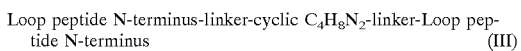
Loop peptide N-terminus-linker-cyclic $C_4H_8N_2$-linker-Loop peptide N-terminus (III)

wherein the linker moiety is designed to link the N-terminus of the Loop peptide to a nitrogen atom of the ring $C_4H_8N_2$ and wherein the "loop peptide" comprises at least an 11-membered peptide compound of formula I (SEQ ID NO:4); wherein $X_1$ is independently Val, Gly or Ala, wherein $X_2$ is Try or Phe, wherein $X_3$ is Arg or Lys, and wherein the two Cys moieties form a disulfide bond to create an 11-amino acid functional peptide having TGF-α activity. Furthermore, the functional peptides of the invention, as described above (e.g., SEQ ID Nos: 4, 5, and 6), having from about 10 to 18 amino acids in length (e.g., 10, 11, 12, 13, 14, 15, 16, 17, or 18 amino acids) wherein $X_{1a}$ is Val, $X_{1b}$ is Gly, $X_{1c}$ is Ala and $X_4$ is Gly and hetero- or homo-dimers of the various TGF-α peptides described herein can be used in the methods of the invention.

The invention further provides a method for treating a neurodegenerative disease with an pharmaceutically active TGF-α57 polypeptide (SEQ ID NO:3), wherein TGF-α57 is a 57 amino acid polypeptide having the formula IV:

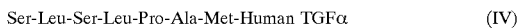
$$Ser-Leu-Ser-Leu-Pro-Ala-Met-Human\ TGF\alpha \quad (IV)$$

wherein human TGFα is a 50 amino acid polypeptide having a sequence as set forth in SEQ ID NO:1.

The invention further provides a method for treating a CNS disease or disorder, wherein the CNS disease or disorder includes CNS ischemia, spinal cord injury, MS, and retinal injury, with a pharmaceutically active TGFα peptide or a TGFα57 polypeptide, wherein the peptide comprises at least an 11-membered peptide compound of formula I (SEQ ID NO:4):

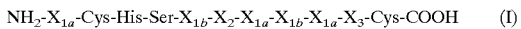
$$NH_2-X_{1a}-Cys-His-Ser-X_{1b}-X_2-X_{1a}-X_{1b}-X_{1a}-X_3-Cys-COOH \quad (I)$$

wherein $X_1$ is independently Val, Gly or Ala, wherein $X_2$ is Try or Phe, wherein $X_3$ is Arg or Lys, and wherein the two Cys moieties form a disulfide bond to create an 11-amino acid functional TGF-α peptide; and wherein TGF-α57 is a 57 amino acid polypeptide having the formula IV:

$$Ser-Leu-Ser-Leu-Pro-Ala-Met-Human\ TGF\alpha \quad (IV)$$

wherein human TGFα is a 50 amino acid polypeptide having the formula of SEQ ID NO:1. Preferably, at least one or more of the following amino acids from formula II are added to the C terminus Cys moiety of formula I:

$$X_4-His-X_{1c}-X_4-X_5-X_6-X_{1c} \quad (II)$$

wherein $X_4$ is Glu or Asp, wherein $X_5$ is Leu or Ile, and wherein $X_6$ is Asp or Glu. Preferably, $X_{1a}$ is Val, $X_{1b}$ is Gly and $X_{1c}$ is Ala. Preferably, $X_2$ is Tyr, and $X_3$ is Arg. Most preferably, the functional peptide is 18 amino acids in length wherein $X_{1a}$ is Val, $X_{1b}$ is Gly, $X_{1c}$ is Ala and $X_4$ is Gly. Furthermore, the functional peptides of the invention, as described above (e.g., SEQ ID Nos: 4, 5, and 6), having from about 10 to 18 amino acids in length (e.g., 10, 11, 12,13, 14,15, 16, 17, or 18 amino acids) wherein $X_{1a}$ is Val, $X_{1b}$ is Gly, $X_{1c}$ is Ala and $X_4$ is Gly and hetero- or homo-dimers of the various TGF-α peptides described herein can be used in the methods for treating a CNS disease or disorder.

The invention further provides a method for enhancing hematopoiesis and myelopoiesis during cytotoxic or immune-suppressing therapy, comprising administering a TGFα polypeptide (SEQ ID NO:1), a TGFα57 polypeptide (i.e., formula IV), a functional TGF-α peptide thereof, or a combination thereof, wherein the peptide comprises at least an 11-membered peptide compound of formula I (SEQ ID NO:4):

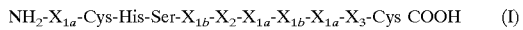

NH$_2$-X$_{1a}$-Cys-His-Ser-X$_{1b}$-X$_2$-X$_{1a}$-X$_{1b}$-X$_{1a}$-X$_3$-Cys COOH   (I)

wherein $X_1$ is independently Val, Gly or Ala, wherein $X_2$ is Try or Phe, wherein $X_3$ is Arg or Lys, and wherein the two Cys moieties form a disulfide bond to create an 11-amino acid functional TGF-α peptide. Preferably, at least one or more of the following amino acids of formula II are added to the C terminus Cys moiety of formula I:

X$_4$-His-X$_{1c}$-X$_4$-Xs-X$_6$-X$_{1c}$   (II)

wherein $X_4$ is Glu or Asp, wherein $X_5$ is Leu or Ile, and wherein $X_6$ is Asp or Glu. Preferably, $X_{1a}$ is Val, $X_{1b}$ is Gly and $X_{1c}$ is Ala. Preferably, $X_2$ is Tyr, and $X_3$ is Arg. Most preferably, the functional peptide is 18 amino acids in length wherein $X_{1a}$ is Val, $X_{1b}$ is Gly, $X_{1c}$ is Ala and $X_4$ is Gly. Furthermore, the functional peptides of the invention, as described above (e.g., SEQ ID Nos: 4, 5, and 6), having from about 10 to 18 amino acids in length (e.g., 10, 11, 12, 13, 14, 15, 16, 17, or 18 amino acids) wherein $X_{1a}$ is Val, $X_{1b}$ is Gly, $X_{1c}$, is Ala and $X_4$ is Gly and hetero-or homo-dimers of the various TGF-α peptides described herein can be used in the methods for enhancing hematopoiesis or myelopoiesis. Preferably, the invention further comprises administering a second hematopoietic growth factor agent to stimulate more mature hematopoietic precursor cells, wherein the second hematopoietic growth factor includes erythropoietin, thrombopoietin, G-CSF (granulocyte colony stimulating factor), and GM-CSF (granulocyte macrophage colony stimulating factor).

The invention further provides a method for treating or preventing mucositis of the gastrointestinal tract caused by cytotoxic or immune-suppressing therapy, comprising administering a TGF-α polypeptide (SEQ ID NO:1), a TGF-α57 polypeptide (i.e., formula IV), a functional TGF-α peptide thereof, or combinations thereof, wherein the peptide comprises at least an 11-membered peptide compound of formula I (SEQ ID NO:4):

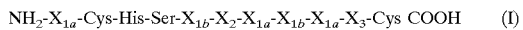

NH$_2$-X$_{1a}$-Cys-His-Ser-X$_{1b}$-X$_2$-X$_{1a}$-X$_{1b}$-X$_{1a}$-X$_3$-Cys COOH   (I)

wherein $X_{1a}$ and $X_{1b}$ are independently Val, Gly or Ala; $X_2$ is Tyr or Phe; $X_3$ is Arg or Lys; and the two Cys moieties are linked via a disulfide bond to form an at least 11-amino acid functional peptide having TGF-α activity. Preferably, at least one or more of the following amino acids are added to the C terminus Cys moiety from formula II:

-X$_4$-His-X$_{1c}$-X$_4$-X$_5$-X$_6$-X$_{1c}$   (II)

wherein $X_4$ is Glu or Asp, wherein $X_5$ is Leu or Ile, and wherein $X_6$ is Asp or Glu. Preferably, $X_{1a}$ is Val, $X_{1b}$ is Gly and $X_{1c}$ is Ala. Preferably, $X_2$ is Tyr, and $X_3$ is Arg. Most preferably, the functional peptide is 18 amino acids in length wherein $X_{1a}$ is Val, $X_{1b}$ is Gly, $X_{1c}$ is Ala and $X_4$ is Gly. Furthermore, the functional peptides of the invention, as described above (e.g., SEQ ID Nos: 4, 5, and 6), having from about 10 to 18 amino acids in length (e.g., 10, 11, 12, 13, 14, 15, 16, 17, or 18 amino acids) wherein $X_{1a}$ is Val, $X_{1b}$ is Gly, $X_{1c}$ is Ala and $X_4$ is Gly and hetero- or homo-dimers of the various TGF-α peptides described herein can be used in the methods for treating or preventing mucositis.

The invention further provides a bifunctional compound that acts as a TGFα mimetic, comprising a compound of formula III:

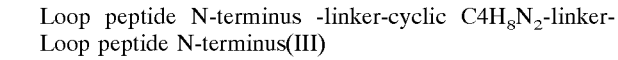

Loop peptide N-terminus -linker-cyclic C$_4$H$_8$N$_2$-linker-Loop peptide N-terminus(III)

wherein the linker moiety is designed to link the N-terminus of the Loop peptide to a nitrogen atom of the ring C$_4$H$_8$N$_2$ and wherein the "loop peptide" comprises at least an 11-membered peptide compound of formula I:

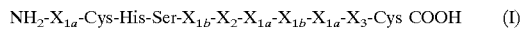

NH$_2$-X$_{1a}$-Cys-His-Ser-X$_{1b}$-X$_2$-X$_{1a}$-X$_{1b}$-X$_{1a}$-X$_3$-Cys COOH   (I)

wherein $X_{1a}$ and $X_{1b}$ are independently Val, Gly or Ala; $X_2$ is Tyr or Phe; $X_3$ is Arg or Lys; and the two Cys moieties are linked via a disulfide bond to form an at least 11-amino acid functional peptide having TGF-α activity. Preferably, at least one or more of the following amino acids are added to the C terminus Cys moiety from formula II:

-X$_4$-His-X$_{1c}$-X$_4$-X$_5$-X$_6$-X$_{1c}$   (II)

wherein $X_4$ is Glu or Asp, wherein $X_5$ is Leu or Ile, and wherein $X_6$ is Asp or Glu. Preferably, $X_{1a}$ is Val, $X_{1b}$ is Gly and $X_{1c}$ is Ala. Preferably, the linker group is independently selected from the group consisting of substituted or unsubstituted C$_{1-6}$ alkyl, substituted or unsubstituted C$_{2-6}$ alkenyl, substituted or unsubstituted C$_{1-6}$ alkoxy, xylenyl, wherein the substitutions are selected from the group consisting of oxo, epoxyl, hydroxyl, chloryl, bromyl, fluoryl, and amino. Preferably, $X_2$ is Tyr, and $X_3$ is Arg. Most preferably, the functional peptide is 18 amino acids in length wherein $X_{1a}$ is Val, $X_{1b}$ is Gly, $X_{1c}$ is Ala and $X_4$ is Gly.

The invention further provides a method for treating inflammatory bowel disease, colitis, and Chron's Disease of the gastrointestinal tract, comprising administering a TGF-α polypeptide (SEQ ID NO:1), a TGF-α57 polypeptide (formula IV), a functional TGF-α peptide thereof, or combinations thereof, wherein the peptide comprises at least an 11-membered peptide compound of formula I:

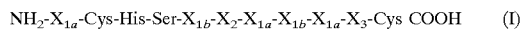

NH$_2$-X$_{1a}$-Cys-His-Ser-X$_{1b}$-X$_2$-X$_{1a}$-X$_{1b}$-X$_{1a}$-X$_3$-Cys COOH   (I)

wherein $X_1$ is independently Val, Gly or Ala, wherein $X_2$ is Try or Phe, wherein $X_3$ is Arg or Lys, and wherein the two Cys moieties form a disulfide bond to create an 11-amino acid functional TGF-α peptide. Preferably, at least one or more of the following amino acids are added to the C terminus Cys moiety from formula II:

-X$_4$-His-X$_{1c}$-X$_4$-X$_5$-X$_6$-X$_{1c}$   (II)

wherein $X_4$ is Glu or Asp, wherein $X_5$ is Leu or Ile, and wherein $X_6$ is Asp or Glu. Preferably, $X_{1a}$ is Val, $X_{1b}$ is Gly and $X_{1c}$ is Ala. Preferably, $X_2$ is Tyr, and $X_3$ is Arg. Most preferably, the functional peptide is 18 amino acids in length wherein $X_{1a}$ is Val, $X_{1b}$ is Gly, $X_{1c}$ is Ala and $X_4$ is Gly. Furthermore, the functional peptides of the invention, as described above (e.g., SEQ ID Nos: 4, 5, and 6), having from about 10 to 18 amino acids in length (e.g., 10, 11, 12, 13, 14, 15, 16, 17, or 18 amino acids) wherein $X_{1a}$ is Val, $X_{1b}$ is Gly, $X_{1c}$ is Ala and $X_4$ is Gly and hetero- or homo-dimers of the various TGF-α peptides described herein can be used in the methods for treating a inflammatory bowel disease, colitis, Chron's Disease and the like.

The invention further provides a method for treating an inflammatory reaction or autoimmune diseases resulting in weight-loss, comprising administering a TGFα polypeptide (SEQ ID NO:1), a TGFα57 polypeptide (formula IV), a functional TGF-α peptide thereof, or combinations thereof, wherein the peptide comprises at least an 11-membered peptide compound of formula I:

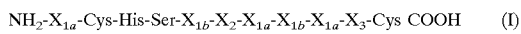

$$NH_2\text{-}X_{1a}\text{-}Cys\text{-}His\text{-}Ser\text{-}X_{1b}\text{-}X_2\text{-}X_{1a}\text{-}X_{1b}\text{-}X_{1a}\text{-}X_3\text{-}Cys\ COOH \quad (I)$$

wherein $X_1$ is independently Val, Gly or Ala, wherein $X_2$ is Try or Phe, wherein $X_3$ is Arg or Lys, and wherein the two Cys moieties form a disulfide bond to create an 11-amino acid functional TGF-α peptide. Preferably, at least one or more of the following amino acids are added to the C terminus Cys moiety from formula II (SEQ ID NO:5):

$$X_4\text{-}His\text{-}X_{1c}\text{-}X_4\text{-}X_5\text{-}X_6\text{-}X_{1c} \quad (II)$$

wherein $X_4$ is Glu or Asp, wherein $X_5$ is Leu or Ile, and wherein $X_6$ is Asp or Glu. Preferably, $X_{1a}$ is Val, $X_{1b}$ is Gly and $X_{1c}$ is Ala. Preferably, $X_2$ is Tyr, and $X_3$ is Arg. Most preferably, the functional peptide is 18 amino acids in length wherein $X_{1a}$ is Val, $X_{1b}$ is Gly, $X_{1c}$ is Ala and $X_4$ is Gly. Furthermore, the functional peptides of the invention, as described above (e.g., SEQ ID Nos: 4, 5, and 6), having from about 10 to 18 amino acids in length (e.g., 10, 11, 12, 13, 14, 15, 16, 17, or 18 amino acids) wherein $X_{1a}$ is Val, $X_{1b}$ is Gly, $X_{1c}$ is Ala and $X_4$ is Gly and hetero-or homo-dimers of the various TGF-α peptides described herein can be used in the methods for treating an autoimmune disease or inflammatory disorder. Preferably, the autoimmune diseases includes Type II (Juvenile) Diabetes, rheumatoid arthritis, lupus, HIV-associated disorders (e.g., AIDS) and multiple sclerosis.

Gene Therapy and Gene Delivery

The TGF-α polypeptides (e.g., SEQ ID NO:1), TGF-α57 polypeptide, and functional TGF-α peptides thereof are particularly suited for delivery to a subject by means of a nucleic acid gene expression system ex vivo or in vivo. A variety of transfection techniques are currently available and used to transfer DNA in vitro into cells; including calcium phosphate-DNA precipitation, DEAE-Dextran transfection, electroporation, liposome mediated DNA transfer or transduction with recombinant viral vectors. Such ex vivo treatment protocols have been used to transfer DNA into a variety of different cell types including epithelial cells (U.S. Pat. No. 4,868,116; Morgan and Mulligan WO87/00201; Morgan et al., 1987, Science 237:1476–1479; Morgan and Mulligan, U.S. Pat. No. 4,980,286), endothelial cells (WO89/05345), hepatocytes (WO89/07136; Wolff et al., 1987, Proc. Natl. Acad. Sci. USA 84:3344–3348; Ledley et al., 1987 Proc. Natl. Acad. Sci. 84:5335–5339; Wilson and Mulligan, WO89/07136; Wilson et al., 1990, Proc. Natl. Acad. Sci. 87:8437–8441) fibroblasts (Palmer et al., 1987, Proc. Natl. Acad. Sci. USA 84:1055–1059; Anson et al., 1987, Mol. Biol. Med. 4:11–20; Rosenberg et al., 1988, Science 242:1575–1578; Naughton & Naughton, U.S. Pat. No. 4,963,489), lymphocytes (Anderson et al., U.S. Pat. No. 5,399,346; Blaese, R. M. et al., 1995, Science 270:475–480) and hematopoietic stem cells (Lim, B. et al. 1989, Proc. Natl. Acad. Sci. USA 86:8892–8896; Anderson et al., U.S. Pat. No. 5,399,346). A summary of typical protocols, methodology, and vectors is provided in "The Development of Human Gene Therapy," Ed. Theodore Friedmann, Cold Spring Harbor Laboratory Press, New York, 1999, the disclosure of which is incorporated herein.

Direct in vivo gene transfer has recently been attempted with formulations of DNA trapped in liposomes (Ledley et al., 1987, J. Pediatrics 110:1); or in proteoliposomes that contain viral envelope receptor proteins (Nicolau et al., 1983, Proc. Natl. Acad. Sci. U.S.A. 80:1068); and DNA coupled to a polylysine-glycoprotein carrier complex. In addition, "gene guns" have been used for gene delivery into cells (Australian Patent No. 9068389). Naked DNA, or DNA associated with liposomes, can be formulated in liquid carrier solutions for injection into interstitial spaces for transfer of DNA into cells (Felgner, WO90/11092).

As described above, polynucleotide sequences encoding a TGF-α polypeptide or function peptide fragment, can be cloned into vectors suitable for delivery to host cells for expression. In particular retroviral vectors containing the polypeptides of the invention are particularly suitable for delivering polynucleotides to cells for gene therapy. Current strategies for gene therapy are reviewed in "The Development of Human Gene Therapy," Ed. Theodore Friedmann, Cold Spring Harbor Laboratory Press, New York, 1999, the disclosure of which is incorporated herein.

Delivery of a polynucleotide of interest may be accomplished in vivo by administration of the vectors to an individual subject, typically by systemic administration (e.g., intravenous, intraperitoneal, intramuscular, subdermal, or intracranial infusion). Alternatively, the vectors may be used to deliver polynucleotides to cells ex vivo such as cells explanted from an individual patient (e.g., tumor-infiltrating lymphocytes, bone marrow aspirates, tissue biopsy) or universal donor hematopoietic stem cells, followed by reimplantation of the cells into a patient, usually after selection for cells which have incorporated the polynucleotide.

The vectors may be used for gene therapy to reduce the incidence of weight-loss and associated disorders resulting from particular diseases (e.g., cancer), or viral diseases (e.g., AIDS, mononucleosis, herpesvirus infection, cytomegalovirus infection, papillomavirus infection) or to modify the genome of selected types of cells of a patient for any therapeutic benefit.

The vectors of the invention can be used to introduce polynucleotides into a variety of cells and tissues including myeloid cells, bone marrow cells, lymphocytes, hepatocytes, fibroblasts, lung cells, epithelial cells and muscle cells. For example, polynucleotides encoding a TGF-α polypeptide may be transferred to stem cells.

Pharmaceutical Composition and Formulations

The invention includes various pharmaceutical compositions useful for delivery or administration of the peptides of the invention. In one embodiment the pharmaceutical composition are useful in treating or preventing weight-loss associated with a disorder or disease. Such disorders or diseases include weight-loss attributable to, for example, chemotherapy or a viral infection (e.g., HIV). The pharmaceutical compositions according to the invention are prepared by bringing a polypeptide or peptide derivative of TGF-α, a TGF-α mimetic into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405–1412, 1461–1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

The pharmaceutical compositions are preferably prepared and administered in dose units. Solid dose units are tablets, capsules and suppositories and including, for example, alginate based pH dependent release gel caps. For treatment of a subject, depending on activity of the compound, manner of administration, nature and severity of the disorder, age and body weight of the subject, different daily doses are necessary. Under certain circumstances, however, higher or lower daily doses may be appropriate. The administration of the daily dose can be carried out both by single administration in the form of an individual dose unit or by several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of particular disorders. Various considerations are described, e.g., in Langer, Science, 249:1527, (1990); Gilman et aL (eds.) (1990), each of which is herein incorporated by reference.

In one embodiment, the invention provides a pharmaceutical composition useful for administering a TGF-α polypeptide or functional fragment, or a nucleic acid encoding a TGF-α polypeptide or functional fragment, to a subject in need of such treatment. "Administering" the pharmaceutical composition of the invention may be accomplished by any means known to the skilled artisan. Preferably a "subject" refers to a mammal, most preferably a human.

The TGF-α polypeptide or functional fragment can be administered parenterally, enterically, by injection, rapid infusion, nasopharyngeal absorption, dermal absorption, rectally and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners and elixirs containing inert diluents commonly used in the art, such as purified water. Where the disease or disorder is a gastrointestinal disorder oral formulations or suppository formulations are preferred.

Sterile injectable solutions can be prepared by incorporating the active agent (see formula I, formula II, or formula III and TGFα) in the required amount (e.g. about 10 µg to about 10 mg/kg) in an appropriate solvent and then sterilizing, such as by sterile filtration. Further, powders can be prepared by standard techniques such as freeze drying or vacuum drying.

In another embodiment, the active agent is prepared with a biodegradable carrier for sustained release characteristics for either sustained release in the GI tract or for target organ implantation with long term active agent release characteristics to the intended site of activity. Biodegradable polymers include, for example, ethylene vinyl acetate, polyanhydrides, polyglycolic acids, polylactic acids, collagen, polyorthoesters, and poly acetic acid. Liposomal formulation can also be used.

The invention will now be described in greater detail by reference to the following non-limiting examples.

EXAMPLE 1

Figure 2:
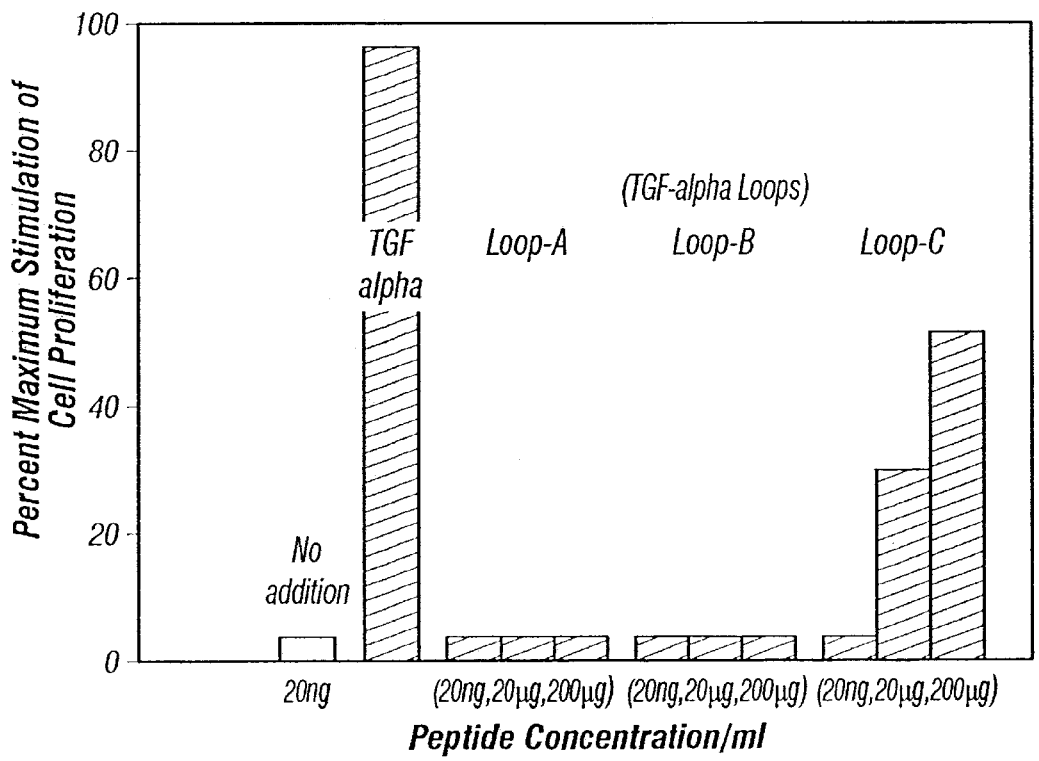
FIG. 2 shows a graph comparing TGFα biological activity of the three loop peptide regions of TGFα (see FIG. 1) wherein Loop A is amino acids 1–21 (starting at the N terminus), Loop B is amino acids 16 to 32 and Loop C is amino acids 33 to 50. Only Loop C showed significant TGFα activity as determined by cell proliferation and in a dose response fashion.

Each of the three loop regions in human TGFα was investigated for TGFα-like biological activity, such as stimulation of cellular proliferation as measured by $^3$H thymidine incorporation of stem cells. As shown in FIG. 2, only the Loop C peptide (corresponding to amino acids 33–50) showed significant TGF-α biological activity as compared to data obtained with TGF-α 50 amino acid polypeptide or even the altered splice 57 amino acid polypeptide and is therefore a TGF-α mimetic peptide. Accordingly, data from TGFα or TGF-α57 show what can be called "TGF-α activity" and that these are predictive of activity of the functional TGF-α peptide and similar functional TGF-α peptides embodied in the genus of formula I with or without the addition of a "tail" region of formula II. These data predict activity for the functional TGF-α peptides when activity is also shown for TGF-α or for TGF-α57.

EXAMPLE 2

Hematopoiesis

Figure 3:
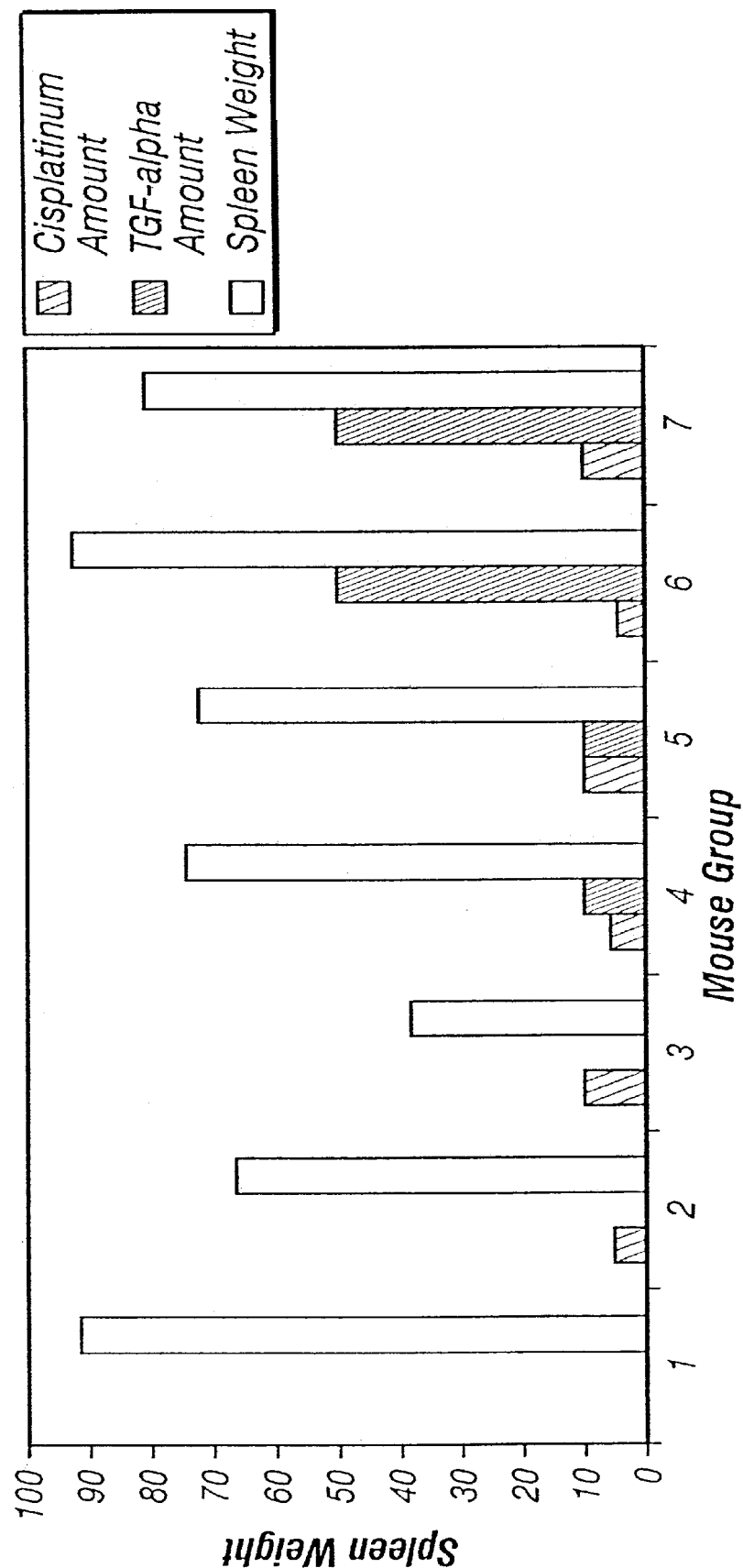
FIG. 3 shows a graph of mouse spleen weights that were treated with Cis Platinum (CP) at either 5 μg/g or 10 μg/g and with TGFα at concentrations of 10 ng/g or 50 ng/g. These data show that TGFα treatment caused a return to normal spleen weights despite CP treatment that reduced spleen weights significantly.

TGF-α and related polypeptides, such as TGF-α57, showed surprising enhancing activity in an in vivo model of general hematopoiesis when administered in conjunction with a potent cytotoxic agent Cis Platinum (CP). FIG. 3 shows a graph of mouse spleen weights that were treated with CP at either 5 µg/g or 10 µg/g and with TGF-α57 at concentrations of 10 ng/g or 50 ng/g. These data show that TGF-α57 treatment caused a return to normal spleen weights despite CP treatment that reduced spleen weights significantly. This in vivo experiment is a predictive model for hematopoiesis in humans as CP is a cytotoxic agent commonly used for cancer chemotherapy that is known to significantly reduce trilineage hematopoietic cells. Hematopoietic and myeloid cells are red blood cell precursors, platelet precursors (megakaryocytes), and immune (white) blood cell precursors of various forms of T cells, B cells and macrophages. Moreover, platelet counts were higher in those mice injected with TGF-α57 (and CP) as opposed to CP alone were such counts were significantly reduced from normal. It should be noted that references to TGF-α as a human 50 amino acid polypeptide further include reference to human TGFα 57 as an alternative variant.

The experiment procedure dosed those animals to be treated with TGFα 57 4 hours prior to challenge with CP. A single dose of CP was administered. Additional doses (as indicated) of TGFα 57 were made at 24 hours, 48 hours, 72 hours and 96 hours after the CP dose. All doses were made by IP injection. Controls were dosed with saline instead of either or both of CP and TGF-α57.

The animals were sacrificed about 4 hours after the last TGF-α57 (or saline) dose. Key organs were removed and spleens were immediately weighed after a clean incision. All the relevant organs were placed in formalin, transported for histopathological analysis, mounted, sectioned, stained and observed. The results of this histological analysis of the spleens for hematopoietic effect and the GI tract (below) provided surprising and unexpected data of the effect of TGF-α57 activity.

H&E-stained spleens of a CP-treated mouse spleen (10 μg/g) showed apoptotic cells (densely stained with fragments of nuclei) in the germinal center (GC). T cells in the central arterial area showed the absence of a marginal zone and much fewer erythrocytes and T cells in the perifolecular area. A normal mouse spleen (no CP and no TGF-α57) fixed in formalin showed an arteriole enriched for T cell progenitors. There was erythrocytes in the perifollicular zone surrounding both the T cell and B cell compartments of white pulp. A mouse spleen treated with CP (10 μg/g) and TGF-α57 (50 ng/g) showed an increased number of T cells and erythrocytes in the perifollicular zone. The T cells stained for the T-cell receptor but were negative for CD4 and CD8 markers. Accordingly, the T-cells are double null T-cell progenitors induced by TGF-α administration.

These in vivo data in a predictive model of hematopoiesis and confirmed by blinded histological analysis (the histologist/pathologist was blinded as to the treatment history of the coded tissues received) providing surprising evidence of the utility of peptides having TGF-α activity to augment hematopoiesis and genesis of immune cells following cytotoxic exposure. These data predict and provide a reasonable correlation that TGF-α and the peptides of formula I, formula II and formula III are useful therapeutic agents for enhancing hematopoiesis following or during cytotoxic therapy, such as cancer treatment. Therefore, a useful method for improving cancer chemotherapy is to combine either TGF-α or a peptide from formula I, formula II, formula III, of formula IV or combinations thereof with cytotoxic treatment regimens to reduce dose-limiting side effects of cytotoxic agents.

An additional experiment investigated TGF-α activity (using TGF-α57) on human bone-marrow enriched CD34 cells. FACS-sorted human CD34 positive and CD38 negative cells were cultured in liquid primary cultures in Iscove's modified Dulbecco's media with supplements. TGFα (57) was added alone (10 ng/ml) and exhibited a 35% increase in CD34 positive progenitor cells. Stem Cell Factor (SCF) was used as a positive control (500 ng/ml) and provided a three-fold increase in CD34 positive cells. When a combination of SCF (500 ng/ml) and TGFα (10 ng/ml) was added, a synergistic 12-fold increase in CD34 positive cells was observed. An unexpected result was the stimulation of the proliferation of dendritic precurso cells in the TGF-α treated cultures.

EXAMPLE 3
Mucositis and Gastrointestinal Diseases

The small intestine comprises the duodenum, jejunum and ileum. It is the principal site for absorption of digestive products from the GI tract. Digestion begins in the stomach and is completed in the small intestine in association with the absorptive process. The intestinal mucosa surface is made up of numerous finger-like projections called villi. In addition, mucosal epithelium between the basis of the villi is formed into the crypts which contain stem cells.

TGFα or a peptide from formula I, formula II, formula III, or formula IV having TGFα activity or combinations thereof are also useful for treating mucositis associated intestinal bleeding, dyspepsia caused by with cytotoxic therapy and for improving the barrier function of the GI tract compromised by cytotoxic therapy. The in vivo experiment with seven groups of mice described above for hematopoietic effects noted in spleens also examined the GI tract of these treated mice. Histological examination of mouse intestines showed the following: CP (single ip dose of 10 μg/g) treated intestine, when cross-sectioned, showed significant injury to the villi. Specifically, the villi are necrotic, the crypts are in irregular shapes, and the tips of the crypts were exhibiting loss of cellular integrity. A cross section of a normal mouse GI tract (no CP and no TGFα57) showed a normal intestinal surface with villi having long and slender mucosal projections with a core of lamina propria covered by a luminal epithelial layer. A single row of intestinal crypt is found at the base of the mucosa. These crypts that lie between adjacent villi are surrounded by the same lamina propria that form the villous cores. Both columnar absorptive cells and goblet cells cover the villous surfaces. The goblet cells contain apical clear vacuoles. A cross section of a mouse intestine exposed to both the CP (10 μg/g) and TGFα57 (50 ng/g) showed that the intestinal structure was very similar to the normal intestinal structure. Specifically, the villus was long and slender. Both absorptive cells and goblet cells were visible at the surface of the villi, and there was an abundant amount of goblet cells on the surface.

A 160×magnification of the intestines of a CP-treated mouse, a normal mouse and a CP treated and TGFα57 treated mouse at the same doses as described above. The CP-treated mouse showed injured villi with degenerating and necrotic tips. Red blood cells were observed in the damaged villi. The crypts were irregularly shaped and in had various heights. The normal mouse showed smooth villi tips of the villi and nuclei of enterocytes were observed throughout the villus. The crypts were similar in height and had a regular shape. The CP treated and TGF-α treated mouse had normal appearing villi as described for the normal mouse. The crypts also appeared normal.

Further CP (10 μg/g) treated without TGF-α57 mice and CP (10 μg/g) and 50 ng/g of TGF-α57 treated mice intestines when examined under higher maginification showed severely injured crypt surfaces in the CP treated mice due to cell death and necrosis. Red cells were visible at the damaged surface indicating intestinal bleeding. In addition, the CP-treated mouse showed a loss of brush borders and very little of a glycocalyx or fuzzy coat. Globlet cells appeared interspersed, necrotic and fewer in number than normal. The effect of TGF-α treatment showed protection of the villa surface. Specifically, the epithelial cells appeared normal with extended brush borders. The nuclei were very densely stained and elongated.

Figure 4:
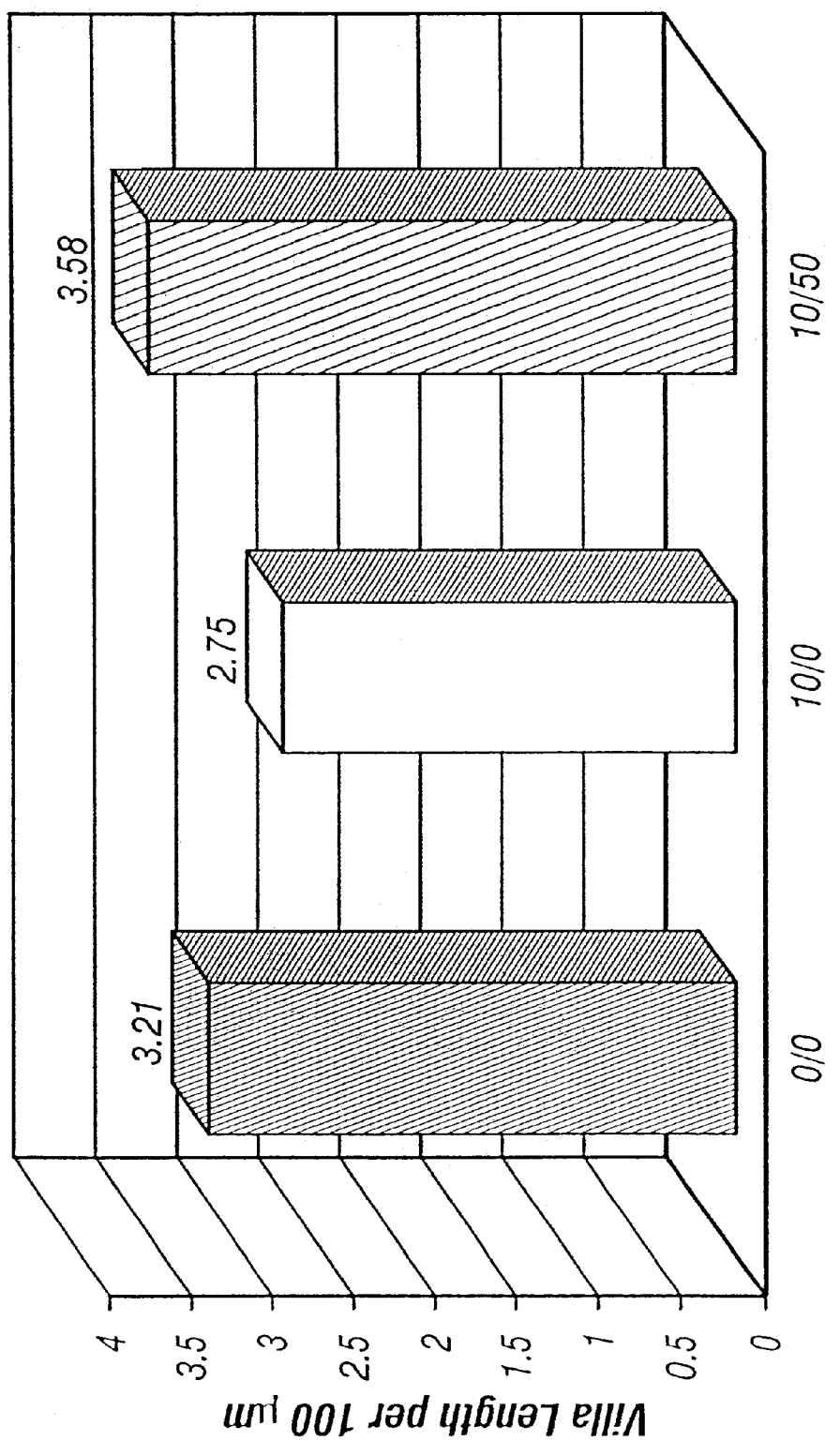
FIG. 4 depicts a summary of histological data that measured average crypt height of the three groups of mice. TGFα 57 treatment (50 ng/g) was able to more-than-restore crypt height loss from CP treatment.

The histological data is summarized in FIG. 4 that measured average crypt height of the three groups of mice. TGFα57 and TGF-α (50 a.a.) treatment (50 ng/g) was able to more-than-restore crypt height loss from CP treatment.

An alcian blue staining method permitted differentiation of absorptive cells and goblet cells. Goblet cell mucus is stained a blue color while the absorptive cells remain less stained. Stains of intestine from normal mice, CP only treated (10 µg/g) and both CP (10 µg/g) and TGFα57 (50 ng/g) treated mice showed significant differences. In the normal intestine each villus extended from the luminal surface to the basal muscularis mucosal surface. Goblet cells were scattered and predominated in the base of the villus whereas columnar absorptive cells lined the luminal surface. In the CP treated mouse, the alcian blue staining showed villi that contained fewer number of goblet cells (than normal). The injured absorptive and goblet cells were degenerating at the tip of the villi and abundant secretory mucus material was stained in the luminal surface. In the CP/TGF-α mouse, there were an increased number of goblet cells scattered throughout the villi. The intestinal villi appeared normal with elongation. The majority of enterocytes did not appear to be alcian blue stained positive. The luminal plasma membranes of the villi were well protected by TGF-α treatment. The number of goblet cells was counted on the average unit length of intestine. TGFα treatment not only increased the number of goblet cells but also increased the number from CP treatment to a higher level than normal intestine.

Accordingly, these data show the effects of TGFα, and the functional peptides having TGF-α activity from formula I, formula II, formula III, and formula IV having therapeutic activity to treat or prevent mucositis associated with cytotoxic drug therapy and for inflammatory bowel diseases. Moreover, the histological effect showing that there was a prevention of mast cell degranulation, provides additional data supporting the gastrointestinal applications for TGFα, and the functional peptides having TGF-α activity of formula I, formula II, formula III, and formula IV.

EXAMPLE 4
Immune Related Diseases

In addition, TGF-α activity resulted in stimulation of proliferation of select immune cells (particularly of the T cell lineage) after administration to mice after immune-suppression of CP administration. The stimulated immune cells were phenotypically identified as CD4 positive T cells and double null CD4 negative CD8 negative T cell progenitors. Thus, TGF-α activity (e.g., from TGFα57 administration) resulted in generation of T-cells with characterisitics that regulated immune functions. Therefore, these data predict that TGFα activity and the functional peptides of formula I, formula II, formula III, and formula IV will be effective in treating autoimmune diseases by mitigating over-inflammatory reactions. The in vivo activity of TGFα (and the functional peptides of formula I, formula II, formula III, and formula IV) to stimulate early T cell progenitors in the release of TH-1 and TH-2 cytokines and this regulation of immune phenomena. The stimulation of select immune cells, in particular cells of a T cell lineage, was seen consistently in the mice who received CP and TGF-α57 in lymphoid tissue, Peyers Patches and the spleen. Further, recruitment of help via CD4 cells in some cases boosts immune system function in general.

TGF-α administration prevented mast cell degranulation and subsequent histamine release. In addition TGF-α has effectes in downregulating TNF-α receptors in vivo and downreglating IL-6 and MIP in vivo, including blockign neutrophil trafficking. This is a parallel activity that is in addition to the gastrointestinal anti-inflammatory activity and prevention of mucositis of TGFα (and the functional peptides of formula I, formula II, formula III, and formula IV) described herein.

EXAMPLE 5

In order to determine the effects of TGF-α polypeptides on weight-loss four groups of rats were tested. The experiment was designed to compare two of the peptides of TGF-α (SEQ ID NO:1 and SEQ ID NO:3) on weight-loss in the presence of a chemotherapeutic drug, cisplatin.

All animals were dosed over a period of 5 days. Group 1 animals received cisplatin at 10 µg/g, Group 2 animals received cisplatin at 10 µg/g plus TGF-α (SEQ ID NO:1) at 50 ng/g; Group 3 animals received cisplatin at 10 µg/g plus TGF-α57 (SEQ ID NO:3) at 50 ng/g; and Group 4 animals received TGF-α (SEQ ID NO:1) at 50 ng/g. Following completion of the dosing protocols animals from each group were measure and organs/tissues were harvested and placed in buffered formalin. The tissues measured included lungs, spleens, kidneys, pancreas, intestines and tongues.

Figure 5:
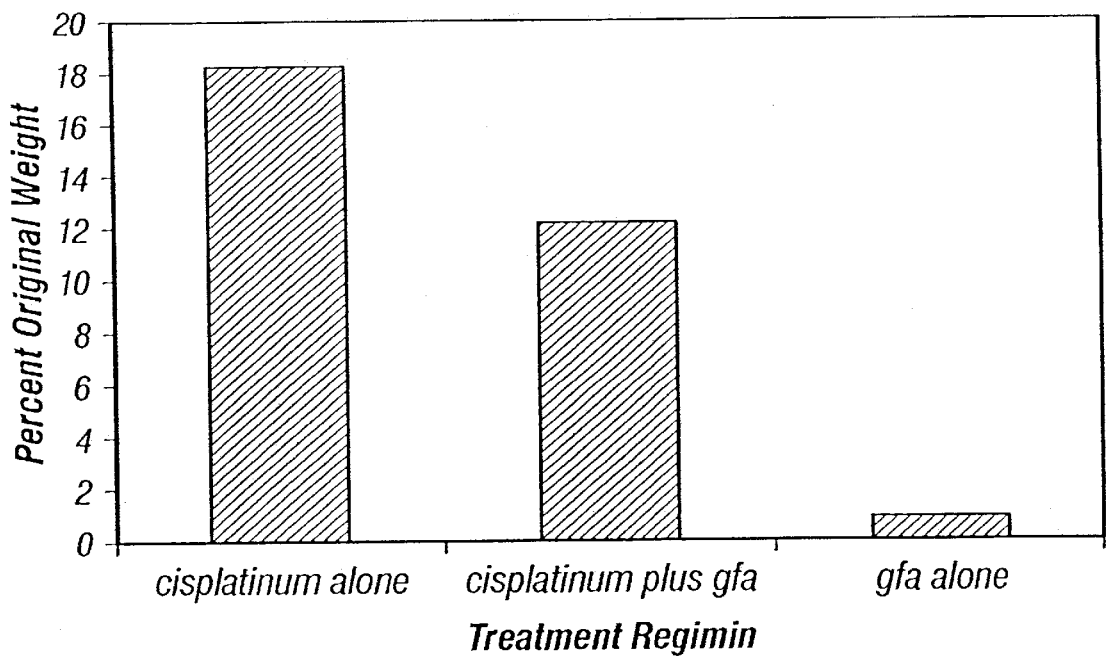
FIG. 5 shows a graph depicting the effects of cisplatinum-alone, cisplatinum and a TGF-α polypeptide, and a TGF-α alone on weight loss of mice.
Figure 6:
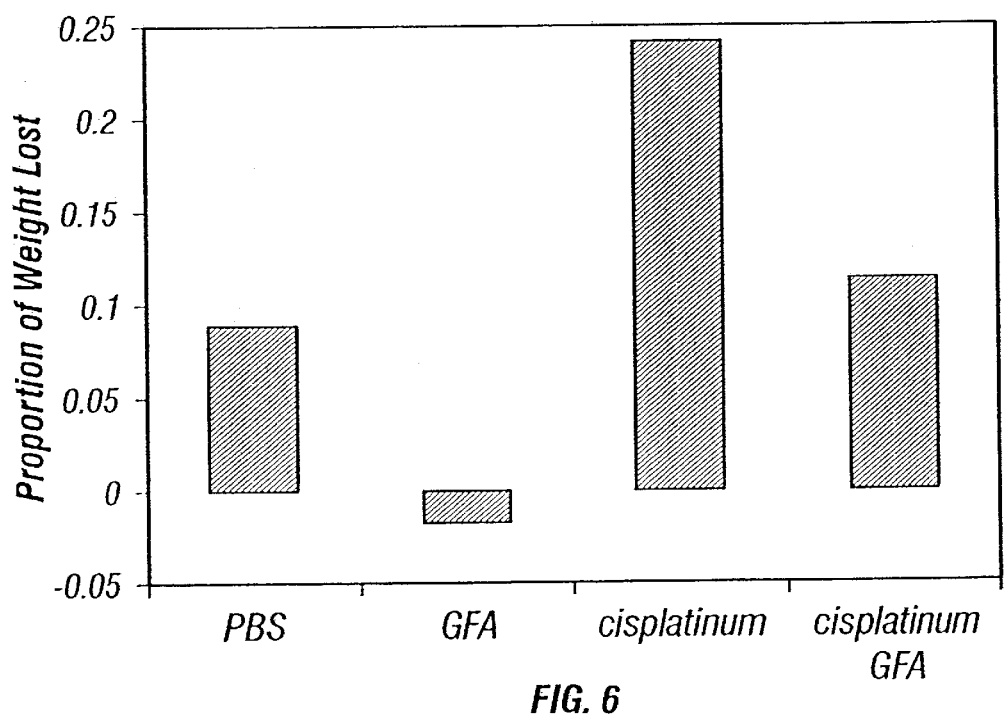
FIG. 6 shows weight loss in mice following cisplatin administration with and without concurrent TGF-α treatment. The graph shows (from left to right) the proportion of weight-loss in the presence of PBS alone, TGF-α alone, cisplatin alone, and cisplatin+TGF-α.

In the 9 animals in group 1 (cisplatin treatment), the average weight loss was 18.3%; in the 13 animals in groups 2 and 3 (cisplatin+TGF) the average weight loss was 12.1%; and in the 6 animals in group 4 (TGF alone) the average weight loss was 0.9% (FIG. 5).

In addition, studies of TGF-α for the treatment of diarrhea in non-human primates was also performed. A 6-year old non-human primate exhibiting chronic inflammatory-like gastrointestinal symptoms was treated with TGF-α at 300 ng/g intraperitoneally once and subsequently 50 ng/g S.C. for 6 days. The primate showed a steady increase in stool consistency and the monkey showed steady weight gain through the treatment period (see Table 1 and 2). This weight gain was maintained at least for several weeks post treatment. In addition, the reduction of SEGs (see column 6, Table 1) neutrophils correlates with reduction in inflammation associated with neutrophil influx and concomitant pro-oinflammatory cytokines. No adverse effects were noted in hematology or serum chemistries, or in the primates attitude, behavior or appetite.

TABLE 1

| Time | wt. | hemo-globin | pcv % | wbc | Seg | Bands | Lymph | Monos | Eos | Basos | Abn. Cells | Platelets | CD4+ | CD8+ | Dual CD8+ CD4+ |
|---|---|---|---|---|---|---|---|---|---|---|---|---|---|---|---|
| 1 | 5.80 | 12.6 | 40.3 | 16.6 | 76% | 0% | 19% | 5% | 0% | 0% | 0% | 543 | 28.4% | 56.3% | 6.7% |
| 2 | 6.33 | 11.1 | 38.0 | 20.2 | 69% | 0% | 20% | 10% | 1% | 0% | 0% | 567 | | | |
| 3 | 6.74 | 9.2 | 32.1 | 10.3 | 61% | 0% | 34% | 4% | 1% | 0% | 0% | 456 | 36.7% | 53.1% | 6.3% |
| 4 | 8.21 | 10.3 | 34.2 | 8.4 | 48% | 0% | 42% | 9% | 1% | 0% | 0% | 534 | 31.3% | 54.0% | 9.1% |
| 5 | 8.93 | 10.8 | 37.1 | 11.2 | 46% | 0% | 45% | 8% | 0% | 1% | 0% | 425 | 33.4% | 49.8% | 8.1% |
| 6 | 9.42 | 11.5 | 38.1 | 15.5 | 56% | 1% | 31% | 11% | 1% | 0% | 0% | 434 | 35.1% | 50.3% | 7.7% |

TABLE 2

| Time | Na⁺ | K⁺ | Cl⁻ | Glu | BUN | Creatine | Total Protein | Albumin | Albumin corrected | Total Billirubin | Ca²⁺ | Alk Phos | ALT (GPT) | AST (GOT) | GGT |
|---|---|---|---|---|---|---|---|---|---|---|---|---|---|---|---|
| 1 | 133 | 3.3 | 87 | 73 | 45 | 0.6 | 8.6 | 4.9 | 5.9 | 1.2 | 11.6 | 103 | 8 | 26 | 57 |
| 2 | 144 | 4.8 | 95 | 51 | 19 | 0.5 | 7.4 | 3.7 | 4.4 | | | | | | |
| 3 | 146 | 4.6 | 107 | 68 | 16 | 0.5 | 7.2 | 2.9 | 3.5 | 0.3 | 9.8 | 116 | 17 | 45 | 89 |
| 4 | 150 | 4.4 | 107 | 50 | 19 | 0.7 | 7.1 | 2.9 | 3.5 | 0.3 | 9.7 | 130 | 25 | 34 | 91 |
| 5 | 148 | 4.0 | 108 | 25 | 18 | 0.6 | 6.6 | 2.5 | 3.0 | 0.2 | 9.1 | 107 | 19 | 37 | 64 |
| 6 | 145 | 3.8 | 108 | 21 | 22 | 0.5 | 7.0 | 2.5 | 3.0 | 0.3 | 9.3 | 113 | 15 | 34 | 58 |

Note: Blood glucose levels are generally well below the normal reference range. This is not an abnormality. Albumin results require a correction factor for non-human primates, which is calculated into the second "Albumin corrected" column.

While the invention has been described in detail with reference to certain preferred embodiments thereof, it will be understood that modifications and variations are within the spirit and scope of that which is described and claimed.

What is claimed is:

1. A method of treating a subject having weight loss or at risk of losing weight due to an associated disease state, or treatment of a disease state comprising administering to the subject a transforming growth factor-alpha (TGF-α) polypeptide with a sequence of SEQ ID NO: 1 or SEQ ID NO: 3 in an effective amount to inhibit or reduce weight-loss in the subject.

2. The method of claim 1, wherein the weight-loss is associated with treatment with of the subject with a chemotherapeutic agent.

3. The method of claim 2, wherein the chemotherapeutic agent is selected from the group consisting of carmustine (BCNU), chlorambucil (LEUKERAN), cisplatin (PLATINOL), Cytarabine, doxorubicin (ADRIAMYCIN), fluorouracil (5-FU), methoxetrate (MEXATE), taxol, CPT111, etoposide, and plicamycin (MITHRACIN).

4. The method of claim 1, wherein the disease is ARC or AIDS.

5. The method of claim 1, wherein the subject is a mammal.

6. The method of claim 5, wherein the mammal is a human.

7. A method of increasing the body weight of a subject due to an associated disease state, or treatment of a disease state comprising administering to the subject prior to, simultaneously with, or substantially following weight-loss a transforming growth factor-alpha (TGF-α) polypeptide with a sequence of SEQ ID NO: 1 or SEQ ID NO: 3 in an effective amount to increase or maintain the weight of the subject.

8. The method of claim 7, wherein the weight-loss is associated with treatment of the subject with a chemotherapeutic agent.

9. The method of claim 8, wherein the chemotherapeutic agent is selected from the group consisting of carmustine (BCNU), chlorambucil (LEUKERAN), cisplatin (PLATINOL), Cytarabine, doxorubicin (ADRIAMYCIN), fluorouracil (5-FU), methoxetrate (MEXATE), taxol, CPT111, etoposide, and plicamycin (MITHRACIN).

10. The method of claim 7, wherein the disease is ARC or AIDS.

11. The method of claim 7, wherein the subject is a mammal.

12. The method of claim 11, wherein the mammal is a human.

* * * * *